(12) United States Patent
Murai

(10) Patent No.: US 11,701,060 B2
(45) Date of Patent: Jul. 18, 2023

(54) BED SYSTEM

(71) Applicant: PARAMOUNT BED CO., LTD, Tokyo (JP)

(72) Inventor: Shinya Murai, Tokyo (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 1101 days.

(21) Appl. No.: 16/349,386

(22) PCT Filed: Mar. 29, 2018

(86) PCT No.: PCT/JP2018/013105
§ 371 (c)(1),
(2) Date: May 13, 2019

(87) PCT Pub. No.: WO2018/198659
PCT Pub. Date: Nov. 1, 2018

(65) Prior Publication Data
US 2019/0328332 A1    Oct. 31, 2019

(30) Foreign Application Priority Data

Apr. 28, 2017   (JP) ................................. 2017-090436

(51) Int. Cl.
*A61B 5/00*      (2006.01)
*A61B 5/0205*    (2006.01)
(Continued)

(52) U.S. Cl.
CPC ............ *A61B 5/6892* (2013.01); *A61B 5/002* (2013.01); *A61B 5/0205* (2013.01); *A61B 5/746* (2013.01);
(Continued)

(58) Field of Classification Search
CPC ..... A61B 5/002; A61B 5/1115; A61B 5/6892; G16H 40/67
See application file for complete search history.

(56) References Cited

U.S. PATENT DOCUMENTS 8,344,860 B2 *   1/2013   Collins, Jr. .......... G08B 25/005
                                                340/286.07
9,182,750 B2 *  11/2015   Rawls-Meehan .... A47C 31/008
(Continued)

FOREIGN PATENT DOCUMENTS

| JP | 2009-240660 | 10/2009 |
| JP | 2010-510832 | 4/2010 |
| JP | 2012-86013  | 5/2012  |

OTHER PUBLICATIONS

International Search Report dated Jul. 3, 2018 in International (PCT) Application No. PCT/JP2018/013105.

*Primary Examiner* — Shirley X Jian
(74) *Attorney, Agent, or Firm* — Wenderoth, Lind & Ponack, L.L.P.

(57) ABSTRACT

According to an embodiment, a bed system includes a plurality of bed devices and a first input/output device capable of communicating with the plurality of bed devices. The first input/output device implements a first operation. During the first operation, the first input/output device receives input of a first set value relating to a first item set in each of the plurality of bed devices. At least one of the first input/output device and the plurality of bed devices implements an operation corresponding to the first set value. Thus, a bed system having improved usability is provided.

15 Claims, 21 Drawing Sheets

(51) Int. Cl.
*A61G 7/018* (2006.01)
*A61G 7/05* (2006.01)
*G05B 19/042* (2006.01)
*G16H 40/67* (2018.01)
*A61B 5/024* (2006.01)
*A61B 5/08* (2006.01)
*A61B 5/11* (2006.01)
*A61B 5/145* (2006.01)

(52) U.S. Cl.
CPC ............ *A61B 5/7425* (2013.01); *A61G 7/018* (2013.01); *A61G 7/05* (2013.01); *G05B 19/042* (2013.01); *G16H 40/67* (2018.01); *A61B 5/024* (2013.01); *A61B 5/0816* (2013.01); *A61B 5/1115* (2013.01); *A61B 5/14532* (2013.01); *A61B 5/4809* (2013.01); *A61B 2560/0475* (2013.01); *A61G 2203/20* (2013.01); *A61G 2203/46* (2013.01); *G05B 2219/2608* (2013.01)

(56) References Cited

U.S. PATENT DOCUMENTS

| | | | |
|---|---|---|---|
| 10,098,593 B2* | 10/2018 | Collins, Jr. | A61G 7/0516 |
| 2008/0126132 A1 | 5/2008 | Warner et al. | |
| 2012/0223821 A1* | 9/2012 | Collins, Jr. | A61G 7/0516 340/286.07 |
| 2013/0289770 A1* | 10/2013 | Rawls-Meehan | A61H 23/02 700/275 |
| 2014/0325760 A1* | 11/2014 | Murai | G08B 3/10 5/616 |
| 2015/0057635 A1 | 2/2015 | Bechtel et al. | |
| 2015/0081335 A1* | 3/2015 | Dixon | H04W 4/029 705/2 |
| 2017/0035370 A1 | 2/2017 | Collins, Jr. et al. | |
| 2019/0021675 A1* | 1/2019 | Gehrke | A47C 17/163 |

\* cited by examiner

FIG. 2

| NOTIFICATION SETTING LIST | BROWSING MODE | | BED DEPARTURE | HEARTBEAT | BREATHING |
|---|---|---|---|---|---|
| 2224 | EDA TOSHIRO BORN JANUARY 1, 1971 | | (OFF) | (OFF) | ▲ 25 BREATHS/MINUTE ▼ 10 BREATHS/MINUTE |
| 01 | | | | | |
| 02 | ISHIMURA NOBORU BORN MARCH 31, 1963 | | (※) | (※) | (※) |
| 03 | FUJIMOTO YASUO BORN SEPTEMBER 15, 1958 | FUNCTION: SITTING UP, 3 SECONDS WEIGHT: LOW (30–45 kg) | (ON) | ▲ 135 BEATS/MINUTE ▼ 45 BEATS/MINUTE | ▲ 25 BREATHS/MINUTE ▼ 10 BREATHS/MINUTE |
| 04 | KUROSAKI HISAYOSHI BORN DECEMBER 3, 1980 | FUNCTION: SITTING ON EDGE OF BED WEIGHT: LOW (30–45 kg) | (ON) | ▲ 135 BEATS/MINUTE ▼ 45 BEATS/MINUTE | ▲ 30 BREATHS/MINUTE ▼ 8 BREATHS/MINUTE |
| 2225 | SAKURADA AKIHIKO BORN JANUARY 12, 1976 | FUNCTION: WAKING UP, 10 SECONDS WEIGHT: LOW (30–45 kg) | (ON) | ▲ 110 BEATS/MINUTE (OFF) | ▲ 30 BREATHS/MINUTE ▼ 8 BREATHS/MINUTE |
| 01 | | | | | |
| 02 | KAMIYA SHOTA BORN JUNE 28, 1972 | FUNCTION: WAKING UP, 10 SECONDS WEIGHT: LOW (30–45 kg) | (ON) | ▲ 135 BEATS/MINUTE ▼ 45 BEATS/MINUTE | ▲ 25 BREATHS/MINUTE ▼ 10 BREATHS/MINUTE |
| 03 | TSUMURA MASAHIRO BORN JULY 10, 1948 | FUNCTION: BED DEPARTURE WEIGHT: LOW (30–45 kg) | (ON) | ▲ 110 BEATS/MINUTE (OFF) | ▲ 30 BREATHS/MINUTE ▼ 8 BREATHS/MINUTE |

[EDIT]

FIG. 8

| USER IDENTIFICATION INFORMATION (I1) | USER INTERFACE DEVICE IDENTIFICATION INFORMATION (IB1) | ATTRIBUTE INFORMATION (IC1) |
|---|---|---|
|  |  |  |
|  |  |  |
|  |  |  |
|  |  |  |

FIG. 20

| NOTIFICATION SETTING LIST | BROWSING MODE | | BED DEPARTURE | HEARTBEAT | BREATHING |
|---|---|---|---|---|---|
| 2224 | 01 | EDA TOSHIRO<br>BORN JANUARY 1, 1971 | OFF | OFF | △ 25 BREATHS/MINUTE<br>▽ 10 BREATHS/MINUTE |
| | 02 | ISHIMURA NOBORU<br>BORN MARCH 31, 1963 | ※ | ※ | ※ |
| | 03 | FUJIMOTO YASUO<br>BORN SEPTEMBER 15, 1958 | FUNCTION: SITTING UP 3 SECONDS<br>WEIGHT: LOW (30-45 kg) | ON △ 135 BEATS/MINUTE<br>▽ 45 BEATS/MINUTE | ON △ 25 BREATHS/MINUTE<br>▽ 10 BREATHS/MINUTE |
| | 04 | KUROSAKI HISAYOSHI<br>BORN DECEMBER 3, 1980 | FUNCTION: SITTING ON EDGE OF BED<br>WEIGHT: LOW (30-45 kg) | ON △ 135 BEATS/MINUTE<br>▽ 45 BEATS/MINUTE | ON △ 30 BREATHS/MINUTE<br>▽ 8 BREATHS/MINUTE |
| 2225 | 01 | SAKURADA AKIHIKO<br>BORN JANUARY 12, 1976 | FUNCTION: WAKING UP 10 SECONDS<br>WEIGHT: LOW (30-45 kg) | ON △ 110 BEATS/MINUTE<br>OFF | ON △ 30 BREATHS/MINUTE<br>▽ 8 BREATHS/MINUTE |
| | 02 | KAMIYA SHOTA<br>BORN JUNE 28, 1972 | FUNCTION: WAKING UP 10 SECONDS<br>WEIGHT: LOW (30-45 kg) | ON △ 135 BEATS/MINUTE<br>▽ 45 BEATS/MINUTE | ON △ 25 BREATHS/MINUTE<br>▽ 10 BREATHS/MINUTE |
| | 03 | TSUMURA MASAHIRO<br>BORN JULY 10, 1948 | FUNCTION: BED DEPARTURE<br>WEIGHT: LOW (30-45 kg) | ON △ 110 BEATS/MINUTE<br>OFF | ON △ 30 BREATHS/MINUTE<br>▽ 8 BREATHS/MINUTE |

EDIT

BED SYSTEM

TECHNICAL FIELD

An embodiment of the present invention relates to a bed system.

BACKGROUND ART

A hospital bed having a graphical user interface connected to a patient-holding structure for holding a patient is available (PTL 1). A plurality of patients are typically cared for in a hospital, a care facility, or the like. Demand exists for a bed system that is easy to use and can be used with a plurality of patients.

CITATION LIST

Patent Literature

[PTL 1] Japanese Patent Application Publication No. 2012-86013

SUMMARY OF INVENTION

Technical Problem

An embodiment of the present invention provides a bed system having improved usability.

Solution to Problem

A bed system according to an embodiment includes a plurality of bed devices and a first input/output device capable of communicating with the plurality of bed devices. The first input/output device implements a first operation. During the first operation, the first input/output device receives input of a first set value relating to a first item set in each of the plurality of bed devices. At least one of the first input/output device and the plurality of bed devices implements an operation corresponding to the first set value.

A bed system according to another embodiment includes a plurality of bed devices and a storage unit. One bed device among the plurality of bed devices includes a bed and a bed input/output unit provided separately to the bed and connected to the bed. The bed input/output unit is capable of acquiring state information. The state information includes at least one of bed state information relating to the bed and user state information relating to the state of a user of the bed. The bed state information includes bed moving part information relating to at least one of a height and an angle of the bed. The user state information includes at least one of vital signs information relating to the user and user behavior information relating to the user. The vital signs information includes information relating to at least one of the blood pressure, the blood oxygen saturation, the blood glucose level, the heart rate, the pulse rate, the respiration rate, the weight, and the body temperature of the user. The user behavior information includes information relating to at least one of bed departure, sleeping, waking up, sitting up, and sitting on the edge of the bed in relation to the user. The storage unit stores at least a part of the state information acquired by the bed input/output unit in association with at least one of identification information specifying the user and identification information specifying the bed input/output unit.

Advantageous Effects of Invention

An embodiment of the present invention can provide a bed system having improved usability.

BRIEF DESCRIPTION OF DRAWINGS

FIG. 2 is a pattern diagram showing an example of a display displayed in a bed system according to a second embodiment.

FIG. 8 is a pattern diagram showing an example of information used in a bed system according to an embodiment.

FIG. 20 is a pattern diagram showing an example of a display screen displayed in a bed system according to an embodiment.

DESCRIPTION OF EMBODIMENTS

Figure 1:
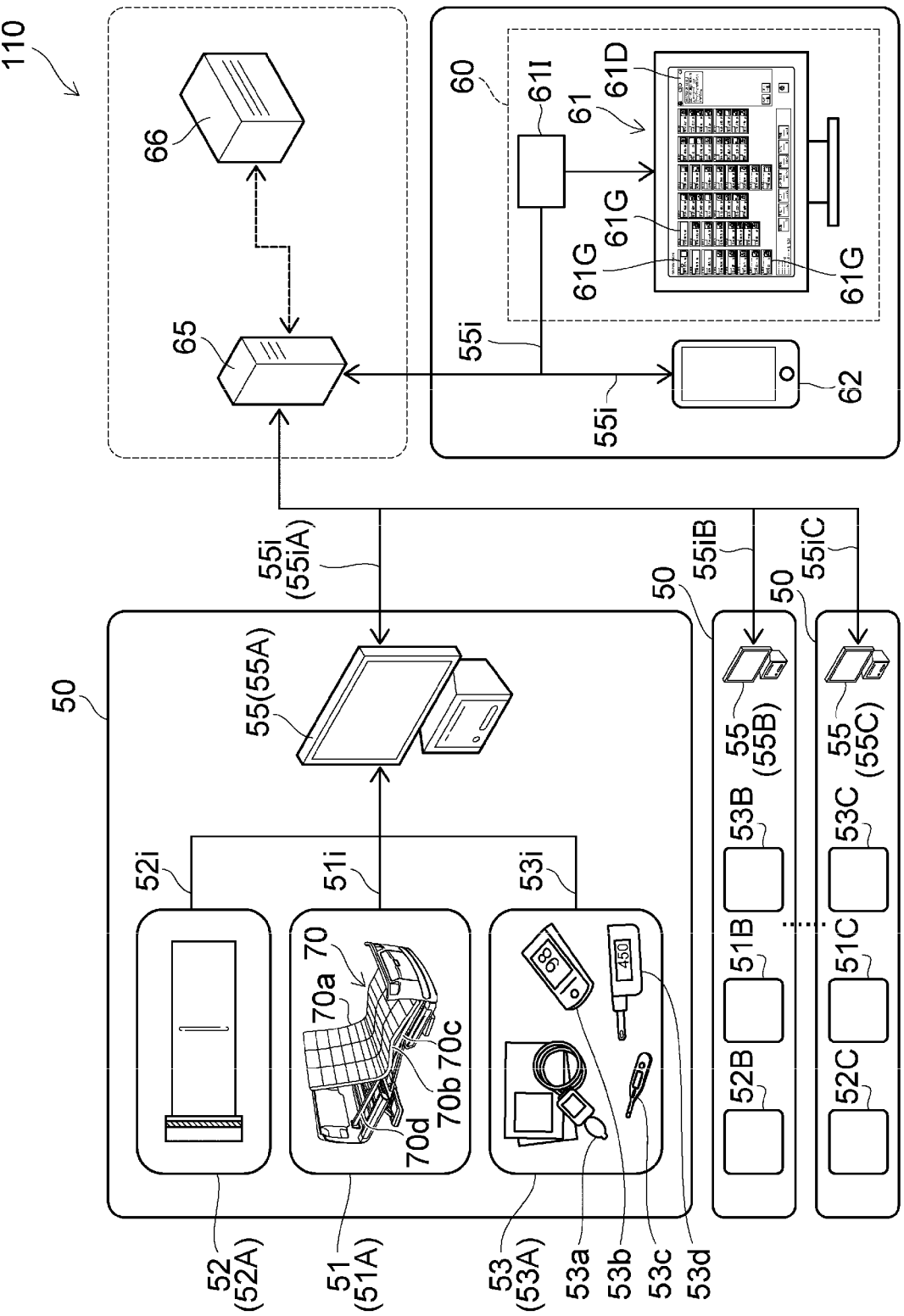
FIG. 1 is a pattern diagram showing an example of a bed system according to a first embodiment.

Embodiments of the present invention will be described below with reference to the figures.

In the description and the figures, identical elements to those appearing in earlier figures have been allocated identical reference numerals, and where appropriate, detailed description thereof has been omitted.

First Embodiment

FIG. 1 is a pattern diagram showing an example of a bed system according to a first embodiment.

As shown in FIG. 1, a bed system 110 according to this embodiment includes a plurality of bed devices 50 and a first input/output device 60. The first input/output device 60 is capable of communicating with the plurality of bed devices 50. The first input/output device 60 is a master station device, for example.

One bed device among the plurality of bed devices 50 includes a bed 51 and a bed input/output unit (a user interface device 55, for example). The bed input/output unit is connected to the bed 51.

The first input/output device 60 includes an acquisition unit 61I and a first display 61, for example. The acquisition unit 61I acquires a plurality of user interface device information 55i. The plurality of user interface device information 55i is acquired from the plurality of user interface devices 55.

The plurality of user interface devices 55 include user interface devices 55A to 55C and so on, for example. The user interface devices 55A to 55C respectively output user interface device information 55iA to 55iC and so on. The plurality of user interface device information 55i (the user interface device information 55iA to 55iC and so on) is supplied to the acquisition unit 61I via a server 65 or the like, for example. The number of user interface devices constituting the plurality of user interface devices 55 is a desired integer no smaller than 2. The number of sets of user interface device information constituting the plurality of user interface device information 55i corresponds to the number of user interface devices constituting the plurality of user interface devices 55.

The acquisition unit 61I is a communication circuit, for example. The acquisition unit 61I includes an electric circuit, for example. The acquisition unit 61I and the plurality of user interface devices 55 exchange information (signals) by a wired or wireless method selected as desired.

The plurality of user interface device information 55i acquired from the plurality of user interface devices 55 may be supplied to an electronic medical record storage unit 66 or the like via the server 65, for example.

The plurality of user interface devices 55 (the user interface devices 55A to 55C and so on) are provided to correspond respectively to the plurality of beds 51 (beds 51A to 51C and so on).

The bed 51 includes a moving part 70, for example. The moving part 70 includes a back section 70a, a knee section 70b, a leg section 70c, a height modifying part 70d (a bed elevator, for example), and so on, for example. By operating the moving part 70, at least one of "back-raising", "knee-raising", "height adjustment", and "inclining" can be performed. "Inclining" includes at least one of rolling and tilting.

An actuator or the like, for example, moves the moving part 70. The moving part 70 may include a sensor (a load sensor, for example), for example. Information relating to the state of a user of the bed 51 may be acquired by detecting a load exerted on the actuator. The user is a patient, a care receiver, or the like, for example. For example, the load sensor or the like provided on the moving part 70 may output information relating to the user (at least one of sitting up, sitting on the edge of the bed, bed departure, and "monitoring", for example). "Monitoring" is a state in which the user remains out of bed continuously for a specified time, for example. When the user remains out of bed continuously for the specified time, the load sensor or the like outputs a signal (information) relating to "monitoring".

Bed moving part information 51i is supplied to the user interface device 55 from each of (one of) the plurality of beds 51. The bed moving part information 51i includes information relating to at least one of the height and the angle of one of the plurality of beds. The bed moving part information 51i includes whether or not the height of the bed 51 is at a minimum, for example. The bed moving part information 51i includes information relating to the angle of at least one of the back section 70a, the knee section 70b, and the leg section 70c, for example. The bed moving part information 51i may also include information relating to the angle of incline of the bed 51.

In this example, the bed 51 is provided with an auxiliary device 52. The auxiliary device 52 is a sheet (or a plate), for example. The auxiliary device 52 is provided between the section of the bed 51 and the mattress, for example. The auxiliary device 52 includes a sensor (at least one of a vibration sensor, a noise sensor, and a force sensor, or the like), for example. The vibration sensor includes an air pressure sensor (a pressure sensor, for example). The auxiliary device 52 is capable of detecting at least one of sleeping, waking up, sitting up, bed departure, monitoring, heart rate, and respiration rate in relation to the user, for example. The detection result is supplied to one of the plurality of user interface devices 55. For example, the sensor included in the auxiliary device 52 detects the user behavior state of the user. The user behavior state includes at least one of bed departure, sleeping, waking up (lying flat in bed), sitting up, and sitting on the edge of the bed in relation to the user of the bed 51. User behavior information 52i including information relating to the user behavior state is supplied to the plurality of user interface devices 55.

The bed 51 may acquire at least a part of the user behavior information 52i. When a sensor is provided in the actuator provided on the bed 51, as described above, the bed 51 may detect the user behavior state (a state including at least one of bed departure, sleeping, waking up, sitting up, and sitting on the edge of the bed). The bed 51 may be considered to include the auxiliary device 52.

In this example, measurement information 53i is also supplied to the user interface device 55. A measurement device 53 acquires the measurement information 53i. The measurement device 53 includes at least one of a blood pressure gauge 53a, a pulse oximeter 53b, a thermometer 53c, and a blood glucose meter 53d, for example. The measurement device 53 acquires information (vital signs information, for example) relating to at least one of the blood pressure, the blood oxygen saturation (SpO$_2$), the blood glucose level, and the body temperature of the user, for example. The blood oxygen saturation is the percutaneous arterial oxygen saturation, for example. The measurement device 53 supplies the vital signs information to the user interface device 55 by communicating with the user interface device 55, for example. This communication is performed by short-range wireless communication, for example. A nurse or the like may input at least a part of the vital signs information into the user interface device 55 manually.

For example, the user interface device 55A (one of the plurality of user interface devices 55) is associated with the bed 51A (one of the plurality of beds 51), an auxiliary device 52A (one of the plurality of auxiliary devices 52), and a measurement device 53A (one of the plurality of measurement devices 53). The user interface device 55B, for example, is associated with the bed 51B, an auxiliary device 52B, and a measurement device 53B. The user interface device 55C, for example, is associated with the bed 51C, an auxiliary device 52C, and a measurement device 53C.

The bed moving part information 51*i*, the user behavior information 52*i*, and the measurement information 53*i*, described above, are supplied to the acquisition unit 61I via the user interface device 55 as the user interface device information 55*i*.

In this example, at least a part of the user interface device information 55*i* is supplied to a second display 62. The second display 62 is a display of a mobile terminal, for example. A caregiver or the like, for example, uses the second display 62. The caregiver or the like provides the respective users of the plurality of beds with nursing care or medical care. For example, each of a plurality of caregivers or the like owns one second display 62.

At least one of the first display 61 and the second display 62 includes a display device (a liquid crystal display device, an EL display device, or the like, for example), for example. The size (the length of the diagonal of the screen, for example) of the first display 61 is greater than the size (the length of the diagonal of the screen, for example) of the second display 62. The acquisition unit 61I may be provided in a casing in which the first display 61 is provided.

Meanwhile, the plurality of caregivers or the like share the first display 61. The first display 61 is provided in a nurse station or the like, for example. The first display 61 is a display of a master station device, for example. The first display 61 is provided in a different position to the plurality of user interface devices 55. The first display 61 is provided in a location (a remote location) apart from the plurality of user interface devices 55. From the display on the first display 61 provided in a remote location, the caregivers or the like can ascertain the states of the beds 51 connected to the plurality of user interface devices 55 or the states of the users of the beds 51.

The first display 61 displays a plurality of images 61G on a single screen 61D on the basis of the plurality of user interface device information 55*i* acquired by the acquisition unit 61I. The plurality of images 61G correspond respectively to the plurality of user interface devices 55.

The single screen 61D displays the plurality of images 61G corresponding respectively to the plurality of user interface devices 55 side by side. The caregivers or the like can thus ascertain the states of the respective users of the plurality of beds 51 efficiently and in an easily understandable manner. As a result, a bed system having improved usability can be provided.

In an embodiment, for example, the state of the user of the bed 51 is detected, and on the basis of the detection result, a report (a notification, a warning, or the like, for example) is issued. The report includes at least one of a display and a sound, for example. The first input/output device 60 issues the report, for example. In this case, the report is issued in relation to the plurality of bed devices 50. Alternatively, the user interface device 55 may issue the report. In this case, one of the plurality of user interface devices 55 issues a report in relation to the user corresponding to that user interface device 55.

A plurality of items are defined as the state of the user of the bed 51, for example. The plurality of items are the heartbeat of the user of the bed 51, the breathing of the user of the bed 51, and so on, for example. The items may also include the user behavior state (bed departure, sleeping, waking up, sitting up, sitting on the edge of the bed, and so on in relation to the user of the bed 51, for example).

These items are measured. The bed device 50 (the bed 51, the auxiliary device 52 of the bed 51, the measurement device 53, and so on) performs this measurement. Measurement results (measurement values) may be provided to the first input/output device 60, the second display 62, and so on as the plurality of user interface device information 55*i*, for example.

A set value (a management value) is determined for each of the plurality of items described above. A report is issued when the measurement value deviates from (exceeds) a range determined in accordance with the set value.

The set values are determined for each of the plurality of users. For example, the set values are determined on the basis of the states (medical conditions and so on) of the plurality of users. The user interface devices 55 corresponding respectively to the plurality of users, for example, can set the set values relating to the plurality of users.

In an embodiment, the first input/output device 60 is capable of setting (inputting) the set values relating to the plurality of users. Thus, the set values can be set (input) more easily than when the user interface devices 55 corresponding respectively to the plurality of users set the set values. As a result, a bed system having improved usability can be provided.

More specifically, in an embodiment, the first input/output device 60 implements a first operation. In the first operation, the first input/output device 60 receives input of a first set value relating to a first item set for each of the plurality of bed devices 50. At least one of the first input/output device 60 and the plurality of bed devices 50 then implements an operation corresponding to the first set value. The operation corresponding to the first set value is issuing a report when the measurement value exceeds the range determined by the first set value, for example. According to this embodiment, a bed system having improved usability can be provided.

Examples of the pluralities of items and set values thereof in the first input/output device 60 will now be described.

FIG. 2 is a pattern diagram showing an example of a display displayed in a bed system according to a second embodiment.

FIG. 2 shows an example of a display on the first display 61 of the first input/output device 60. The first display 61 has a browsing mode and an editing mode, for example. FIG. 2 shows an example of a browsing mode display 61B.

The browsing mode display 61B includes a table. A column for identification information I1 and columns for the plurality of items (a first item 31, a second item 32, and so on) are provided on the browsing mode display 61B.

The identification information I1 specifies the user (a subject user) of one bed (a subject bed 51) among the plurality of beds 51. The identification information I1 includes the name of the subject user, for example. In this example, the column of the identification information I1 displays the date of birth of the user as well as the name of the user. In this example, the column of the identification information I1 displays the ward number of the user and the number of the user within the ward.

In this example, the column of the first item 31 includes a column 31*a* for "heartbeat" and a column 31*b* for "breathing". A column for "bed departure" is provided as the column of the second item 32.

For example, a cell 32B for a set value relating to "bed departure", a cell 31*a*B for a set value relating to "heartbeat", and a cell 31bB for a set value relating to "breathing" are displayed in relation to "user number 01 on ward 2225". Each of the cells is surrounded by two vertical lines and two horizontal lines, for example. The lines do not have to be displayed.

The cell 32B of the set value relating to "bed departure" displays a pictogram (a drawing of a bell and the characters "ON") indicating that a notification operation is in an ON state, for example. In addition, "function: awake for 10 seconds" and "weight: low (30 to 45 kg)" are displayed. The display "function: awake for 10 seconds" indicates that the notification operation is to be performed when the user remains awake for 10 seconds or more. The state of the user is detected in accordance with the weight of the user, for example. By setting (inputting) information (data) relating to the weight of the user, detection is performed appropriately. In this example, the weight of the user is set at "low (30 to 45 kg)".

The cell 31aB of the set value relating to "heartbeat" displays a pictogram (a drawing of a bell and the characters "ON") indicating that the notification operation is in an ON state. In addition, a combination of an upward-pointing triangle and "110 beats per minute" is displayed. This combined display indicates that the set value (the management value) of an upper limit relating to heartbeat is "110 beats per minute". In other words, the notification operation is performed when the heartbeat measurement value exceeds 110 beats per minute. A combination of a downward-pointing triangle and "OFF" is also displayed in the cell 31aB. This combined display indicates that a set value (a management value) of a lower limit relating to heartbeat has not been set. Thus, at least one of an upper limit set value and a lower limit set value may be set for at least one of the plurality of items, for example.

The pictogram in the cell 31aB is surrounded by a yellow line (in FIG. 2, displayed as a thick line), for example. The yellow line indicates that a "notification display", described below, is to be displayed when the measurement value exceeds the range determined by the set value (the management value).

The cell 31bB of the set value relating to "breathing" displays a pictogram (a drawing of a bell and the characters "ON") indicating that the notification operation is in an ON state. In addition, a combination of an upward-pointing triangle and "30 breaths per minute" is displayed. This combined display indicates that the set value (the management value) of an upper limit relating to breathing is "30 breaths per minute". In other words, the notification operation is performed when the breathing measurement value exceeds 30 breaths per minute. A combination of a downward-pointing triangle and "8 breaths per minute" is also displayed in the cell 31bB. This combined display indicates that the set value (the management value) of a lower limit relating to breathing is "8 breaths per minute". In other words, the notification operation is performed when the breathing measurement value falls below 8 breaths per minute.

The pictogram in the cell 31bB is surrounded by a red line (in FIG. 2, displayed as a thicker line than the line in the cell 31aB), for example. The red line indicates that a "warning display", described below, is to be displayed when the measurement value exceeds the range determined by the set value (the management value).

In the example shown in FIG. 2, set values relating to "bed departure" and "heartbeat" are not set for "user number 01 on ward 2224", but a set value relating to "breathing" is set. Hence, in a single bed device 50 (corresponding to a single user), a set value may be set for one of the plurality of items while a set value is not set for another item.

In the example shown in FIG. 2, no set values have been set for the user corresponding to number "02" on "ward 2224".

Hence, a "notification setting list" is displayed on the browsing mode display 61B shown in FIG. 2. The browsing mode display 61B also displays an "edit" button 61Ba (a region for receiving input), for example. When the button 61Ba receives input from an input/output device (a mouse, a touch panel, or the like), for example, the first display 61 shifts to the editing mode.

Figure 3:
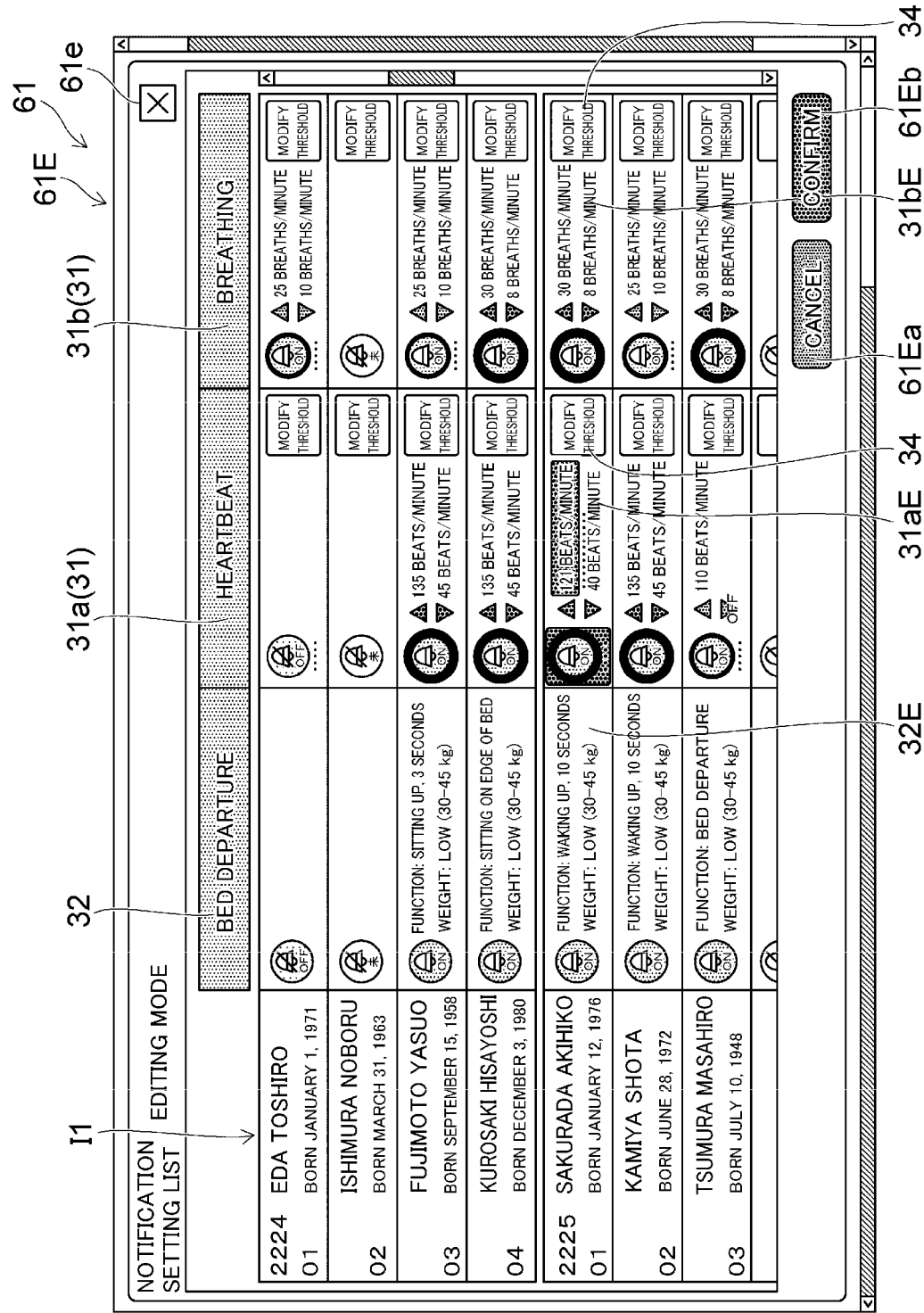
FIG. 3 is a pattern diagram showing an example of a different display screen displayed in the bed system according to the first embodiment.

FIG. 3 is a pattern diagram showing an example of a different display screen displayed in the bed system according to the first embodiment.

FIG. 3 shows an example of an editing mode display 61E. The editing mode display 61E includes a table. A column for the identification information I1 and columns for the plurality of items (the first item 31, the second item 32, and so on) are likewise provided on the editing mode display 61E. In this example also, the column of the first item 31 includes the column 31a for "heartbeat" and the column 31b for "breathing". A column for "bed departure" is provided as the column of the second item 32.

For example, a cell 32E for the set value relating to "bed departure", a cell 31aE for the set value relating to "heartbeat", and a cell 31bE for the set value relating to "breathing" are displayed in relation to "user number 01 on ward 2225".

In this example, the set value (the management value) relating to "bed departure" cannot be set (input) on the first input/output device 60. The set value (the management value) relating to "bed departure" can be set (input) on the user interface devices 55 of the plurality of bed devices 50.

On the other hand, the set value relating to "heartbeat" and the set value relating to "breathing" can be set (input) on the first input/output device 60.

The cell 31aE of the set value relating to "heartbeat" is provided with a "modify threshold" button 34 (a region for receiving input). When the button 34 receives input from the input/output device (a mouse, a touch panel, or the like), for example, the set value (the threshold) relating to "heartbeat" in the cell 31aE enters an editing state. For example, the color of the "121 beats per minute" display relating to "heartbeat" changes. For example, the color changes to red or the like. Alternatively, the display may change to a "flashing display", an "inverted display", or the like. When the upward-pointing triangle button receives input in the editing state, the numeral relating to heartbeat increases. When the downward-pointing triangle button receives input in the editing state, the numeral relating to heartbeat decreases. For example, a cursor may be displayed in the position of "121 beats per minute" and a "value" may be input using a keyboard or the like.

By pressing the "modify threshold" button 34 when the upper limit set value (the threshold) relating to heartbeat reaches a desired value, for example, the lower limit set value (the threshold) relating to heartbeat enters an editing state. By pressing the "modify threshold" button 34 after the lower limit set value (the threshold) relating to heartbeat has been set at a desired value, setting (input) of the set value relating to "heartbeat" is completed.

The cell 31bE of the set value relating to "breathing" is also provided with the "modify threshold" button 34 (a region for receiving input). The set value relating to "breathing" enters the editing state in accordance with the "modify threshold" button 34. The set value relating to "breathing"

(at least one of the upper limit and the lower limit) is set (input) in a similar manner. When the "modify threshold" button 34 receives further input, editing (setting or input) of the set value relating to "breathing" is completed.

The editing mode display 61E shown in FIG. 3 displays a "cancel" button 61Ea (a region for receiving input) and a "confirm" button 61Eb (a region for receiving input). When the "cancel" button 61Ea receives input from the input/output device (a mouse, a touch panel, or the like), for example, the edited (input) set value is canceled and the original state is re-established. When the "confirm" button 61Eb receives input from the input/output device (a mouse, a touch panel, or the like), for example, the first display 61 shifts to the browsing mode display 61B. The edited (set or input) set values can then be checked on the browsing mode display 61B.

The browsing mode display 61B and the editing mode display 61E shown in FIGS. 2 and 3 display an end button 61e (a region for receiving input). When the end button 61e receives input from the input/output device (a mouse, a touch panel, or the like), for example, the first display 61 returns to another screen (a home screen, a notification display screen, or the like, for example). Examples of other screens will be described below.

In this example, as described above, the first input/output device 60 does not receive input of the second set value relating to the second item 32 (in this example, "bed departure"). The second set value relating to the second item 32 is input on the plurality of bed devices 50 (the plurality of user interface devices 55, for example). The second item 32 is set while viewing the state of the user or the state of the bed 51, for example. Thus, the second set value can be set more appropriately. On the other hand, the first set value relating to the first item 31 can be set appropriately even when set (input) on the first input/output device 60 provided in a location apart from the plurality of bed devices 50. The first item 31 and the second item 32 may be distinguished by this difference.

For example, the user interface device 55 (a bed input/output unit) is capable of receiving input of the first set value of the first item 31 of one of the plurality of bed devices 50 and input of the second set value of the second item 32 of that bed device 50. The first input/output device 60 is capable of receiving input of the first set value of the first item 31 in relation to the plurality of bed devices 50. The first input/output device 60 does not receive input of the second set value of the second item 32 in relation to the plurality of bed devices 50. Alternatively, as will be described below, the first input/output device 60 can receive input of the second set value of the second item 32 in relation to the plurality of bed devices 50, but an operation based on the received second set value is not implemented until a condition described below is satisfied.

By ensuring that the first set value of the first item 31 can be set (input) on the first input/output device 60 in relation to the plurality of bed devices 50, a bed system that is easy to use is obtained. Moreover, by ensuring that either the second item 32, which is preferably set near each of the plurality of bed devices 50, cannot be set on the first input/output device 60 or an operation is not performed using the input value as is, the user can be provided with more appropriate medical or nursing care.

In an embodiment, the first item 31 relates to at least one of the heartbeat and the breathing of the user of the bed 51. The heartbeat and the breathing of the user are acquired from the bed 51 or the auxiliary device 52 of the bed 51.

The second item 32, meanwhile, relates to user behavior information including at least one of bed departure, sleeping, waking up, sitting up, and sitting on the edge of the bed in relation to the user of the bed 51.

As described above, the first set value of the first item 31 is input on each of the plurality of bed devices 50 (each of the plurality of user interface devices 55). The first set value of the first item 31 is also input on first input/output device 60. In this case, setting may be performed on a plurality of terminals simultaneously, and as a result, a collision may occur.

In an embodiment, in such a case, a display indicating that the first set value is being input on another input/output device may be displayed on the first input/output device 60 or the plurality of user interface devices 55 (bed input/output units). Alternatively, when the user interface device 55 (the bed input/output unit) receives input of a different set value relating to the first item 31 while the first input/output device 60 is implementing the first operation (receiving input of the first set value relating to the first item 31), at least one of the first input/output device 60 and the plurality of bed devices 50 implements an operation (issues a notification or a warning) corresponding to the different set value. As a result, a collision is avoided, for example.

For example, a notification display, a warning display, or the like, to be described below, is performed as the operation corresponding to the set value. A notification sound, a warning sound, or the like, for example, may be generated as the operation corresponding to the set value. The operation corresponding to the set value is performed on the basis of comparison results between the ranges determined in accordance with the management values (the thresholds) of the first set value relating to the first item 31, the second set value relating to the second item 32, and so on, and the measurement values relating to these items. An example of the operation corresponding to the set value will be described below.

Second Embodiment

In this embodiment, the first input/output device 60 receives input of the second set value. The configuration of the bed system according to the first embodiment is applied as the configuration of the bed system according to this embodiment. The browsing mode display 61B according to this embodiment is similar to the browsing mode display 61B according to the first embodiment, for example. The editing mode display 61E according to this embodiment differs from the editing mode display 61E according to the first embodiment, for example. An example of the editing mode display 61E according to this embodiment will be described below.

Figure 4:
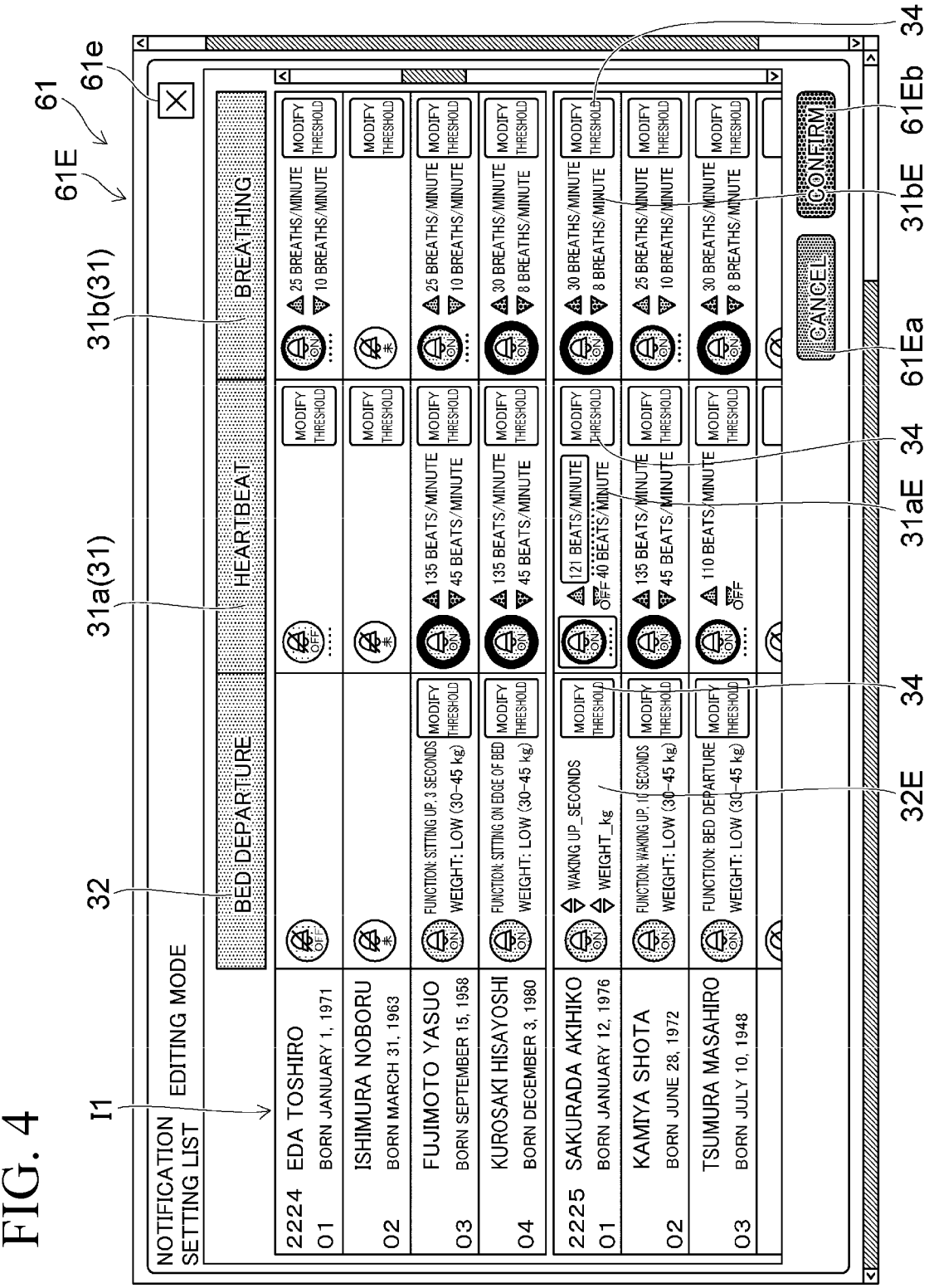
FIG. 4 is a pattern diagram showing an example of a display screen displayed in the bed system according to the second embodiment.

FIG. 4 is a pattern diagram showing an example of a display screen displayed in the bed system according to the second embodiment.

FIG. 4 shows an example of the editing mode display 61E according to this embodiment. Likewise in this example, a column for the identification information I1 and columns for the plurality of items (the first item 31, the second item 32, and so on) are provided on the editing mode display 61E. The column of the first item 31 includes the column 31a for "heartbeat" and the column 31b for "breathing". A column for "bed departure" is provided as the column of the second item 32. In this embodiment, the cell 31aE of the set value relating to "heartbeat" and the cell 31bE of the set value relating to "breathing" are similar to the corresponding cells of the first embodiment (see FIG. 3). In this embodiment, the cell 32E of the set value relating to "bed departure" differs from the corresponding cell of the first embodiment (see FIG. 3).

As shown in FIG. 4, the cell 32E of the set value relating to "bed departure" is provided with the "modify threshold" button 34 (a region for receiving input). When the button 34 receives input from the input/output device (a mouse, a touch panel, or the like), for example, the set value (the threshold) relating to "bed departure" in the cell 32E enters the editing state.

For example, the duration of an "awake" state used to determine "bed departure" can be input. For example, when the upward-pointing triangle button receives input in the editing state, the duration increases. When the downward-pointing triangle button receives input in the editing state, the duration decreases. For example, a cursor may be displayed in a position between "awake" and "seconds", and a "value" relating to the duration may be input using a keyboard or the like.

As shown in FIG. 4, the "weight" of the user, which is used to detect "bed departure", may be input, for example. For example, when the upward-pointing triangle button receives input in the editing state, the "weight" increases. When the downward-pointing triangle button receives input in the editing state, the "weight" decreases. For example, a cursor may be displayed in a position between "weight" and "kg", and a "value" relating to the weight may be input using a keyboard or the like.

When the "modify threshold" button 34 in the cell 32E of the set value relating to "bed departure" receives further input, for example, editing (setting or input) of the set value relating to "bed departure" is completed.

Hence, in this embodiment, the second set value relating to the second item 32 can be input from the first display 61 of the first input/output device 60.

Accordingly, the first input/output device 60 is capable of implementing a second operation in addition to the first operation described above. In the second operation, the first input/output device 60 implements a non-reception operation or a reception operation. In the non-reception operation, the first input/output device 60 does not receive input of the second set value relating to the second item 32, which is set in each of the plurality of bed devices 50 (first embodiment). As described above, even in a case where the first input/output device 60 implements the non-reception operation, the first input/output device 60 can display the second set value, set on at least one of the plurality of bed devices 50, on the browsing mode display 61B, for example.

In the reception operation, meanwhile, the first input/output device 60 receives input of the second set value (second embodiment). When the first input/output device 60 implements the reception operation, a confirmation operation is performed rather than using the input second set value as is. For example, when at least one of the plurality of bed devices 50 receives approval of the second set value following the reception operation, at least one of the first input/output device 60 and the plurality of bed devices 50 implements an operation (issues a notification, a warning, or the like) corresponding to the second set value. Likewise in a case where the first input/output device 60 implements the reception operation, the first input/output device 60 can display the second set value, set on at least one of the plurality of bed devices 50, on the browsing mode display 61B, for example.

The second item 32 is a parameter that is preferably confirmed ultimately at the bedside, for example. In a remote location, for example, viewing a parameter of this type, which is preferably confirmed ultimately at the bedside, is permitted, but setting (inputting) thereof is prohibited (first embodiment). Alternatively, in a case where a parameter that is preferably confirmed ultimately at the bedside is edited (or input) in a remote location, the parameter is not used immediately, and instead, the caregiver or the like is required to acquire the value thereof at the bedside and then determine whether or not to use the value (i.e. approve use of the value) (second embodiment).

An example of approval of the second set value will now be described. For example, when the "confirm" button 61Eb on the editing mode display 61E shown in FIG. 4 receives input, editing on the first input/output device 60 is terminated. Next, a message or the like, for example, is displayed on the screen of one of the user interface devices 55 of the plurality of bed devices 50. The second set value corresponding to that bed device 50 is then edited (set or input) on the first input/output device 60.

Figure 5:
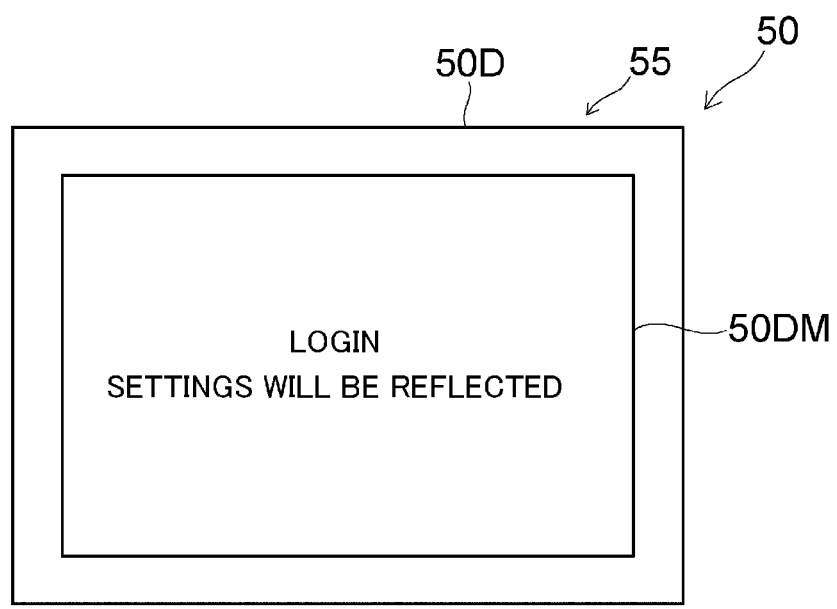
FIG. 5 is a pattern diagram showing an example of a display screen displayed in the bed system according to the second embodiment.

FIG. 5 is a pattern diagram showing an example of a display screen displayed in the bed system according to the second embodiment.

FIG. 5 shows an example of a message 50DM displayed on the display 50D of the user interface device 55 (the bed device 50) after the editing mode display 61E according to this embodiment.

As shown in FIG. 5, "login" and "settings will be reflected" are displayed as the message 50DM, for example. Hence, when the first input/output device 60 implements the reception operation (receives input of the set value of the second setting item), at least one of the plurality of bed devices 50 issues a notification (displays the message 50DM or the like, for example) prompting the approval of implementation of an operation corresponding to the second set value. The notification may be issued by sound (including voice or the like), for example.

In response to the notification prompting approval, the caregiver or the like of the user of the bed 51 approves implementation of an operation (issuing a notification, a warning, or the like, for example) using the second set value after confirming the state of the bed 51 and the state of the user. By not performing an operation using the input value as is, the user can be provided with more appropriate medical or nursing care.

In this embodiment, a notification indicating that an operation (issuing a notification, a warning, or the like) corresponding to the second set value will not be implemented may be issued prior to approval. For example, in one example, the first input/output device 60 may issue a notification indicating that "the second set value has not yet been approved" in the reception operation (on the editing mode display 61E or the like, for example). This notification may include a display in which the color (and flashing state) or the like of the cell 32E of the set value relating to "bed departure" is different to the color (and flashing state) of the other cells (the cell 31aE, the cell 31bE, or the like), for example. The notification may also include issuing a message (a display, a sound, or the like) when editing of the cell 32E of the set value relating to "bed departure" is completed. In one example, for example, the first input/output device 60 may issue a notification indicating that "the second set value has not yet been approved" on the browsing mode display 61B or the like, for example. By issuing this notification, the fact that "the second set value has not yet been approved" is clarified. As a result, an improvement in usability can be achieved.

The first set value of the first item 31 and the second set value of the second item 32 are set in relation to the plurality of bed devices 50 (the plurality of users) using the editing mode display 61E shown in FIG. 3 or 4, for example.

When a bed device that is not connected to the first input/output device 60 exists at this time, the first display 61 of the first input/output device 60 may not display information relating to the unconnected bed device. For example, the bed system 110 may include a separate bed device not connected to the first input/output device 60. The separate bed device is the bed device including the user interface device 55C, for example. The user interface device 55C is not yet connected to the first input/output device 60. In this case, the first input/output device 60 may display information relating to the plurality of bed devices 50 on a single screen without displaying information relating to the separate bed device on the single screen.

Thus, when a bed device that is not connected to the first input/output device 60 exists, for example, a clearer display is realized than if information relating to that bed device is displayed.

For example, when information relating to the plurality of bed devices 50 is displayed, the plurality of setting information described above (the first set value, the second set value, and so on) is displayed in one small region. By not displaying information relating to an unconnected bed device at this time, the display can be made clearer.

In an embodiment, when inputting the set value of the first item 31, a reference range may be determined in relation to the input value. The reference range is determined in a facility in which the plurality of bed devices 50 are provided, for example. When the input value deviates from the reference range, for example, there may be an error in the input value. By issuing a notification when the input value deviates from the reference range, the inputter (the caregiver or the like, for example) is more likely to notice the error.

For example, when the value set (input) into the cell 31aE of the set value relating to "heartbeat", for example, on the editing mode display 61E shown in FIG. 3 exceeds a determined range, the cell 31aE or a part of the cell 31aE (the numeral exceeding the range or the like) flashes. Alternatively, the cell 31aE or a part of the cell 31aE changes color. Thus, it is easier to see that the input value deviates from the reference range. When there is an error in the input value, the error can be noticed more easily.

Hence, the first input/output device 60 may issue a notification when at least one of the first set value of the first item 31 and the second set value of the second item 32 exceeds a reference range. As a result, an improvement in usability is achieved.

In the first and second embodiments described above, the first input/output device 60 acquires measurement values (the plurality of user interface device information 55i shown in FIG. 1, for example) from the plurality of bed devices 50. The first input/output device 60 then issues a report as an operation corresponding to the set values. For example, the first input/output device 60 acquires the first measurement value relating to the first item 31 (at least a part of one set of the plurality of user interface device information 55i) from one of the plurality of bed devices 50 in which the first set value of the first item 31 is set. In this case, the operation corresponding to the first set value includes issuing a report when the corresponding measurement value exceeds the range determined by the first set value. For example, the first input/output device 60 acquires the second measurement value relating to the second item 32 (a different part of one set of the plurality of user interface device information 55i) from one of the plurality of bed devices 50 in which the second set value of the second item 32 is set. In this case, the operation corresponding to the second set value includes issuing a report when the corresponding measurement value exceeds the range determined by the second set value. The report includes at least one of a notification and a warning, for example. The report includes at least one of a display and a sound, for example. The first input/output device 60 issues the report. The second display 62 (a mobile terminal, for example) may issue the report. The respective user interface devices 55 of the plurality of bed devices 50 may also issue the report.

An example of the report issued by the first input/output device 60 will now be described.

Figure 6:
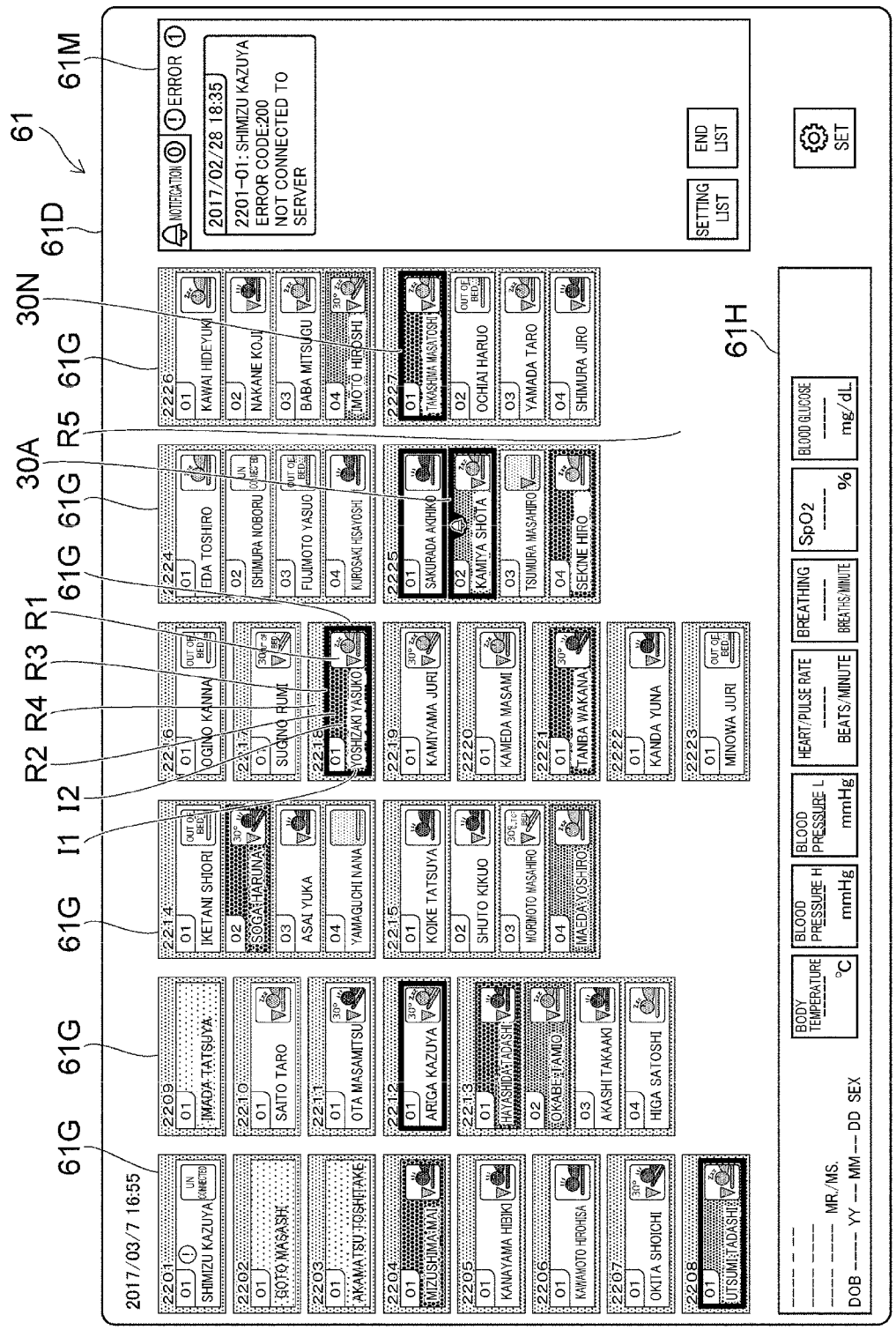
FIG. 6 is a pattern diagram showing an example of a screen displayed in a bed system according to an embodiment.

FIG. 6 is a pattern diagram showing an example of a screen displayed in a bed system according to an embodiment.

FIG. 6 shows an example of a screen 61D displayed on the first display 61. As shown in FIG. 6, the single screen 61D displays the plurality of images 61G side by side. In this example, a message is displayed in a message region 61M. For example, the message is a communication state error or the like, for example.

One of the plurality of images 61G includes a first partial region R1, a second partial region R2, and a third partial region R3. In this example, an outer edge partial region R4 is further provided. The outer edge partial region R4 is provided on the periphery of the first partial region R1, the second partial region R2, and the third partial region R3. The plurality of images 61G are displayed within a background region R5 of the single screen 61D. The outer edge partial region R4 clarifies a boundary between the background region R5 and the image 61G.

For example, the background region R5 is white, for example. The outer edge partial region R4 is a pale color (pale blue or the like), for example.

At least a part of the second partial region R2 is positioned between the first partial region R1 and the third partial region R3. For example, the third partial region R3 is positioned around the first partial region R1 and the second partial region R2. The third partial region R3 is frame-shaped, for example.

One of the plurality of images 61G corresponds to one of the plurality of user interface devices 55 (a subject user interface device 55). In other words, one of the plurality of images 61G corresponds to one set of the plurality of user interface device information 55i. The subject user interface device 55 corresponds to one bed 51 (the subject bed 51) and one user (the subject user). Accordingly, one of the plurality of images 61G corresponds to the subject bed 51 and the subject user. One of the plurality of images 61G will be described below.

The first display 61 displays a pictogram in the first partial region R1, for example. The first display 61 displays the identification information I1 specifying the user in at least a part of the second partial region R2. The first display 61 displays a warning display 30A in the third partial region R3. Examples of these displays will be described below.

A pictogram is displayed in the first partial region R1. The pictogram includes a state display corresponding to the state information (at least one of the bed state information and the user state information). The pictogram includes the bed moving part information 51i, for example. As described above, the bed moving part information 51i includes information relating to at least one of the height and the angle of one of the plurality of beds 51. For example, the pictogram includes a pattern (including characters) corresponding to the height of the subject bed 51. For example, the pictogram includes a pattern (including characters) corresponding to the angle of the subject bed 51. The pictogram includes the user state information (for example, the vital signs information and the user behavior information). The pictogram forms at least a part of the state information.

The identification information I1 is displayed in the second partial region R2. In this example, vital signs information I2 is also displayed in the second partial region R2. The identification information I1 specifies the user (the subject user) of one bed (the subject bed 51) among the plurality of beds 51. The identification information I1 includes the name of the subject user, for example. The vital signs information I2 includes information relating to the vital signs of the subject user. The vital signs information I2 includes information relating to at least one of the blood pressure, the blood oxygen saturation, the blood glucose level, the heart rate, the pulse rate, the respiration rate, the weight, and the body temperature of the subject user.

For example, the identification information I1 includes character information (the characters of the name and so on). The vital signs information I2 is displayed according to color. More specifically, in the second partial region R2, the color of the region, excluding the identification information I1, is modified on the basis of the vital signs of the subject user. Thus, the vital signs information I2 may be displayed according to the color on the periphery of the identification information I1. As a result, the condition (the vital signs) of the subject user can be recognized more easily while ensuring that the identification information I1 remains easy to see. An example of display of the vital signs information I2 according to color will be described below.

Hence, the first display 61 displays the identification information I1 and the vital signs information I2 in the second partial region R2. The vital signs information I2 forms at least a part of the state information.

Meanwhile, the warning display 30A is displayed in the third partial region R3. The warning display 30A is displayed when a specific condition is satisfied. When the state information is abnormal, the warning display 30A is displayed in the third partial region R3 of one of the plurality of images 61G. For example, the first display 61 displays the warning display 30A when at least one of bed departure by the subject user, the heartbeat of the subject user, and the breathing of the subject user is in an abnormal state. The first display 61 may also display the warning display 30A in the third partial region R3 when the bed state information is abnormal.

A reference (a threshold) for determining whether or not an abnormal state has occurred may be determined in accordance with the state (the condition and so on) of the subject user, for example. For example, when the bed 51 or the auxiliary device 52 of a user who finds walking difficult detects that the user is out of bed, a serious accident such as the user falling from the bed 51 may occur. In this case, a rapid response is necessary. In such cases, the warning display 30A is displayed after detecting the bed departure state. In contrast, when bed departure is detected in relation to a user who finds walking easy, the possibility of a serious accident is comparatively low. In such cases, the warning display 30A need not be displayed even after detecting the bed departure state.

The reference for determining whether or not an abnormal state has occurred may be determined on the basis of a combination of the state of the subject user and the state of the bed 51 or the like, for example. When the bed departure state is detected in relation to a user who finds walking difficult and whose bed 51 is high, the user may fall from the high bed 51. In such cases, the warning display 30A is displayed.

The auxiliary device 52 (or the bed 51) or the like detects information relating to heartbeat and breathing continuously, for example. As a result, information relating to the steady heartbeat and breathing of the subject user accumulates. When a dramatic variation from the steady heartbeat and breathing is observed, the warning display 30A is displayed. When the degree of variation is intermediate, a notification display 30N to be described below may be displayed.

In this example, the notification display 30N is displayed in the third partial region R3. For example, the first display 61 may also display the notification display 30N when at least one of the heartbeat of the subject user and the breathing of the subject user varies so as to exceed a reference.

For example, the heartbeat of the subject user and the breathing of the subject user are acquired from the subject bed 51 (one of the plurality of beds) or the auxiliary device 52 of the subject bed 51 (one of the plurality of beds). As described above, the auxiliary device 52 may be considered part of the bed 51.

The heartbeat of the subject user and the breathing of the subject user are detected continuously. When the continuously detected heartbeat or breathing varies so as to exceed a reference (when an event occurs), the condition of the user may have deteriorated. By displaying the notification display 30N when such evidence of deterioration is found, appropriate countermeasures can be taken rapidly.

The reference used to determine whether or not to display the notification display 30N is determined in accordance with the state of the subject user, for example. A looser reference than the reference used to determine whether or not the display the warning display 30A, for example, is employed as the reference (the threshold) for determining whether or not to display the notification display 30N. For example, a nurse or the like prioritizes care of a user for whom the warning display 30A is displayed over care of a user for whom the notification display 30N is displayed.

By displaying the warning display 30A, the nurse or the like can easily identify the user (the care-receiver) having the highest priority. Further, by displaying the notification display 30N, the nurse or the like can easily identify the user (the care-receiver) having the second highest priority. As a result, the quality of medical or nursing care can be improved, for example.

In this example, a window region 61H is provided on the single screen 61D. At least a part of the information relating to one of the plurality of users, for example, is displayed in the window region 61H. In this example, information relating to the body temperature, the blood pressure (the systolic blood pressure and the diastolic blood pressure), the heartbeat (the pulse), the breathing, the $SpO_2$, and the blood glucose is displayed. By clicking (touching) one of the plurality of images 61G, for example, the information relating to the subject user corresponding to that image 61G is displayed in the window region 61H.

Hence, when one of the plurality of images 61G receives input, the first display 61 may display the information corresponding to that image 61G. This information forms at least a part of the information relating to the subject user corresponding to the image 61G, for example. The information corresponding to this one image among the plurality of images 61G may be displayed in a part of the single screen 61D, for example (in the window region 61H, for example). By providing the window region 61H on the same screen 61D, the warning display 30A can be presented to a nurse or the like even while the caregiver or the like is viewing the information displayed in the window region 61H, for example. As a result, cases in which the warning display 30A and so on are overlooked can be suppressed.

In an embodiment, the window region 61H may be provided on a separate screen. For example, when one of the plurality of images 61G receives input, the single screen 61D may shift to a different screen. In this case, a different screen can be used, and therefore information relating to the subject user can be displayed in detail.

Figure 7A:
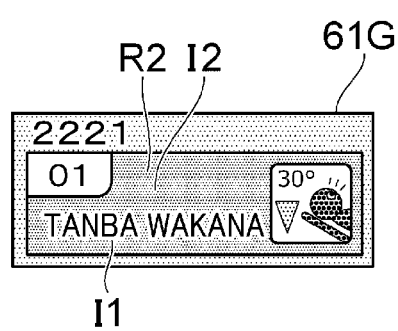
FIGS. 7(a) to 7(c) are pattern diagrams showing examples of images displayed in a bed system according to an embodiment.
Figure 7B:
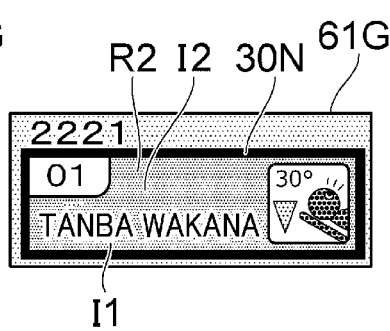
Figure 7C:
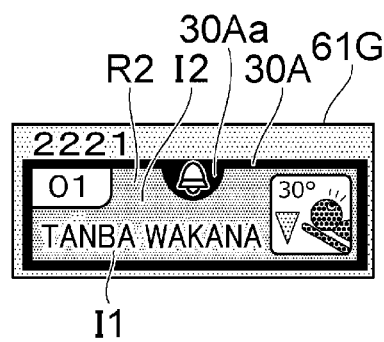

FIGS. 7(a) to 7(c) are pattern diagrams showing examples of images displayed in a bed system according to an embodiment.

FIG. 7(a) shows a state in which no information is displayed in the third partial region R3. FIG. 7(b) shows a state in which the notification display 30N is displayed in the third partial region R3. FIG. 7(c) shows a state in which the warning display 30A is displayed in the third partial region R3.

As shown in FIG. 7(a), when no information is displayed in the third partial region R3, the state of the third partial region R3 is identical to the state of at least a part of the second partial region R2. For example, the color of the third partial region R3 is the same as the color of the vital signs information I2 in the second partial region R2.

The recognizability of the notification display 30N shown in FIG. 7(b) is higher than the recognizability of the vital signs information I2 in the second partial region R2, for example. The color of the notification display 30N is dark red, for example. The vital signs information I2, on the other hand, is displayed in a pale color (pale pink, pale yellow, pale green, pale blue, or the like, for example). The notification display 30N can thus be recognized more easily.

An attention-alerting property (the recognizability) of the warning display 30A shown in FIG. 7(c) is higher than the attention-alerting property (the recognizability) of the notification display 30N, for example. For example, the warning display 30A may include flashing. The notification display 30N, on the other hand, does not flash. The warning display 30A includes a distinctively shaped pattern 30Aa, for example. The distinctively shaped pattern 30Aa is not provided in the notification display 30N. In this example, the distinctively shaped pattern 30Aa is displayed in the shape of a "bell". Due to the distinctively shaped pattern 30Aa, the surface area of the warning display 30A is larger than the surface area of the notification display 30N. Thus, the warning display 30A has at least one of a larger surface area than the notification display 30N and a different pattern to the pattern included in the notification display 30N, for example. As a result, the attention-alerting property of the warning display 30A is higher than the attention-alerting property of the notification display 30N.

The color of the warning display 30A may be different to the color of the notification display 30N. For example, the warning display 30A is dark red. The notification display 30N may have a red color that is paler than the color of the warning display 30A. For example, the chroma of the warning display 30A may be higher than the chroma of the notification display 30N.

As shown in FIG. 7(c), the region displaying the distinctively shaped pattern 30Aa forming a part of the warning display 30A is considered part of the third partial region R3. As shown in FIGS. 7(a) and 7(b), when the warning display 30A is not displayed, this part of the third partial region R3 is identical to the state of at least a part of the second partial region R2. For example, the color of this part of the third partial region R3 is the same as the color of the vital signs information I2 in the second partial region R2.

An example of a user interface device according to an embodiment will now be described.

FIG. 8 is a pattern diagram showing an example of information used in a bed system according to an embodiment.

As shown in FIG. 8, user information I0 (for example, a user information record) includes, for example, the identification information I1 (user identification information) specifying the user of a bed and identification information (user interface device identification information IB1) specifying a bed input/output unit. The identification information I1 (the user identification information) specifying the user of the bed is associated with the identification information (the user interface device identification information IB1) specifying the bed input/output unit.

In this example, attribute information IC1 is also provided as the user information I0. The attribute information IC1 is information relating to the user. The attribute information IC1 includes, for example, the sex of the user, the age of the user, the address (or contact information) of the user, and so on. The attribute information IC1 is associated with the user interface device identification information IB1, for example.

The information shown in FIG. 8 is stored in a storage unit provided in the bed system, for example.

The bed system 110 (see FIG. 1, for example) according to an embodiment is provided with the plurality of bed devices 50 and a storage unit. The storage unit may be provided in a desired location. An example of the storage unit will be described below.

As described above, one (each) of the plurality of bed devices 50 includes the bed 51 and the bed input/output unit (for example, the user interface device 55). The bed input/output unit is connected to the bed 51. The bed input/output unit is a separate component to the bed 51. The bed input/output unit is provided separately to the bed 51 (or components (such as a side rail and a frame) included in the bed 51). By providing the user interface device 55 separately to the bed 51, a combination of the user interface device 55 and the bed 51 can be modified, for example. In so doing, various situations can be responded to easily. As a result, an improvement in usability can be achieved. For example, when the user of the bed 51 moves from one ward to another ward, as will be described below, the user interface device 55 of the user may be moved from the pre-movement ward to the post-movement ward.

The bed input/output unit (for example, the user interface device 55) is capable of acquiring the state information. The state information includes, for example, at least one of the bed state information relating to the bed 51 and the user state information relating to the state of the user of the bed 51. The bed state information includes the bed moving part information. The bed moving part information is information relating to at least one of the height and the angle of the bed 51. The user state information includes at least one of the vital signs information of the user and the user behavior information of the user. The vital signs information includes information relating to at least one of the blood pressure, the blood oxygen saturation, the blood glucose level, the heart rate, the pulse rate, the respiration rate, the weight, and the body temperature of the user. The user behavior information includes information relating to at least one of bed departure, sleeping, waking up, sitting up, and sitting on the edge of the bed in relation to the user. The state information includes the measurement information 53i acquired by the measurement device 53, for example. The state information includes the user behavior information 52i acquired by the auxiliary device 52 or the bed 51.

The storage unit stores at least a part of the state information acquired by the bed input/output unit (the user interface device 55, for example) in association with at least one of the identification information I1 specifying the user and the identification information (the user interface device identification information IB1) specifying the bed input/output unit.

Hence, in an embodiment, the user interface device 55 collects information relating to the bed 51 and information relating to the user of the bed 51, for example. The collected information is supplied to a terminal device or the like such as the server 65, the electronic medical record storage unit 66, the first input/output device 60, or the second display 62. The collected information may be stored in a storage unit provided in a terminal device or the like such as the server 65, the electronic medical record storage unit 66, the first input/output device 60, or the second display 62. The collected information may also be stored in a storage unit provided in the user interface device 55.

By collecting information (bed information and user information) relating to one bed 51 in this manner, the association between the information (data) can be modified easily when the combination of the bed 51 and the user of the bed 51 changes, for example.

For example, a typical nurse call system is not provided with a function for updating user information. Therefore, when the combination of the bed 51 and the user of the bed 51 changes, for example, a delay may occur in modification of the association (the connection, for example) between the bed 51 and the user thereof. When modification of the association between the bed 51 and the user is delayed, for example, the measured user state information may be recorded mistakenly.

In an embodiment, however, at least a part of the state information acquired by the bed input/output unit (the user interface device 55, for example) is stored in association with at least one of the identification information I1 specifying the user and the identification information (the user interface device identification information IB1) specifying the bed input/output unit. As a result, the measured user state information is stored in the correct association.

In an embodiment, the user interface device 55 displays the identification information I1 of the user and the user interface device identification information IB1. As a result, it is easy to see whether or not the association between the information is correct.

Figure 9:
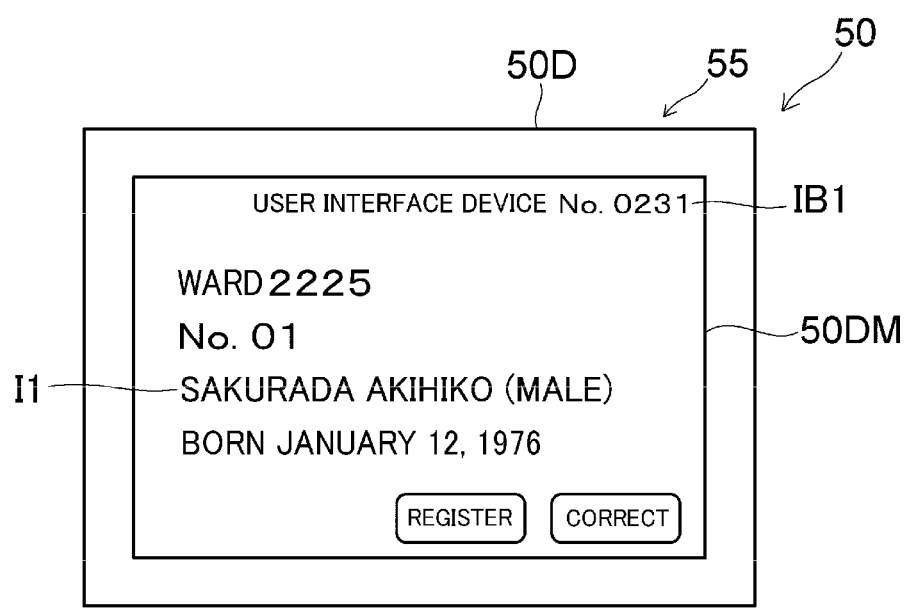
FIG. 9 is a pattern diagram showing an example of a display displayed in a bed system according to an embodiment.

FIG. 9 is a pattern diagram showing an example of a display displayed in a bed system according to an embodiment.

FIG. 9 is an example of a display screen of the bed input/output unit (the user interface device 55, for example). FIG. 9 shows an example of a message 50DMA displayed on the display 50D of the user interface device 55. As shown in FIG. 9, the bed input/output unit is capable of displaying the identification information I1 specifying the user and the identification information (the user interface device identification information IB1) specifying the bed input/output unit. As a result, it is possible to recognize easily whether or not the correct user corresponds to the bed input/output unit (the user interface device 55). Moreover, when an error occurs in the relationship, the error can be corrected.

For example, the bed input/output unit implements an operation prompting approval of the correspondence relationship between the identification information I1 specifying the user and the identification information (the user interface device identification information IB1) specifying the bed input/output unit. In this case, a display (a "register" button) prompting approval of the correspondence relationship is displayed. When the "register" button receives input, the displayed correspondence relationship is stored. If the correspondence relationship is to be corrected, input is performed on a "correct" button, for example. In this case, a correction screen is displayed, and correction is performed thereon, for example. Alternatively, a notification or the like is issued to a manager of the bedside system. As a result, data (information) based on the correct correspondence relationship is received.

Hence, in an embodiment, for example, when new user information is acquired, the user information is connected to information specifying the user interface device 55. A staff member is then prompted to approve this connection on the user interface device 55. Thus, when a difference occurs in the correspondence relationship between the acquired user state information and the actual user of the bed 51, for example, the difference can be corrected.

Following approval, the user information and so on (sensor information, input information, or the like) acquired by the user interface device 55 is stored in connection with the approved user identification information I1. For example, the approved data are supplied to the electronic medical record storage unit 66 or the like.

By employing this bed input/output unit (the user interface device 55, for example), a bed system having improved usability can be provided.

An example in which the settings of the user interface device 55 are modified when the user of the bed 51 moves from one ward to another ward will now be described. For example, the user interface device 55 is capable of modifying identification information of the pre-movement ward to identification information of the post-movement ward and so on. As described above, the identification information I1 specifying the user and the identification information (the user interface device identification information IB1) specifying the bed input/output unit (the user interface device 55, for example) are associated. By modifying the ward identification information in relation to the user interface device 55, for example, movement of the user to another ward is stored (set) as information.

FIGS. 10(a) to 10(d), FIGS. 11(a) to 11(d), and FIG. 12 are pattern diagrams showing examples of displays displayed in a bed system according to an embodiment.

These figures show displays displayed by the display 50D of the user interface device 55 during modification of the settings of the user interface device 55. In this example, the user of the bed 51 moves from ward "2201" to ward "0501".

Figure 10A:
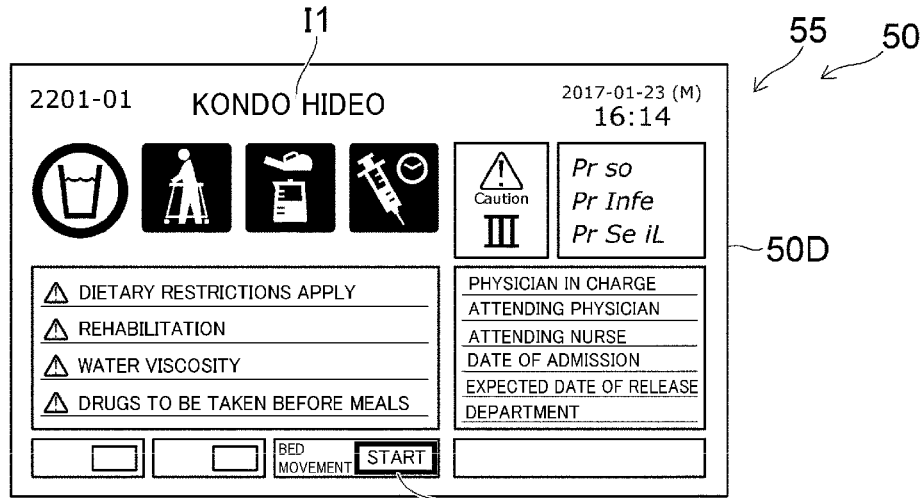
FIGS. 10(a) to 10(d) are pattern diagrams showing examples of displays displayed in a bed system according to an embodiment.
Figure 10B:
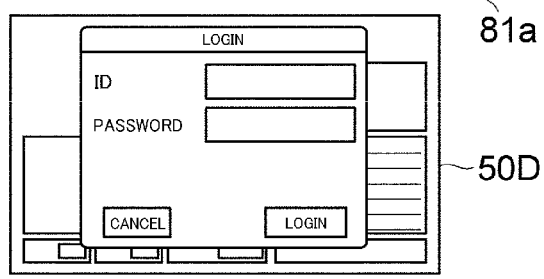
Figure 10C:
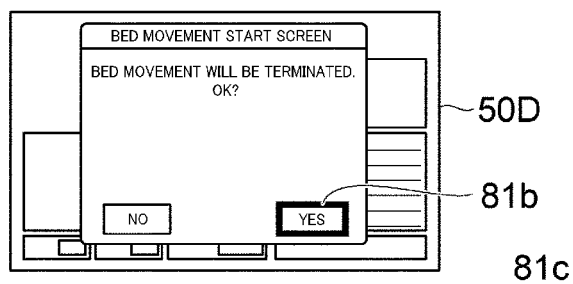
Figure 10D:
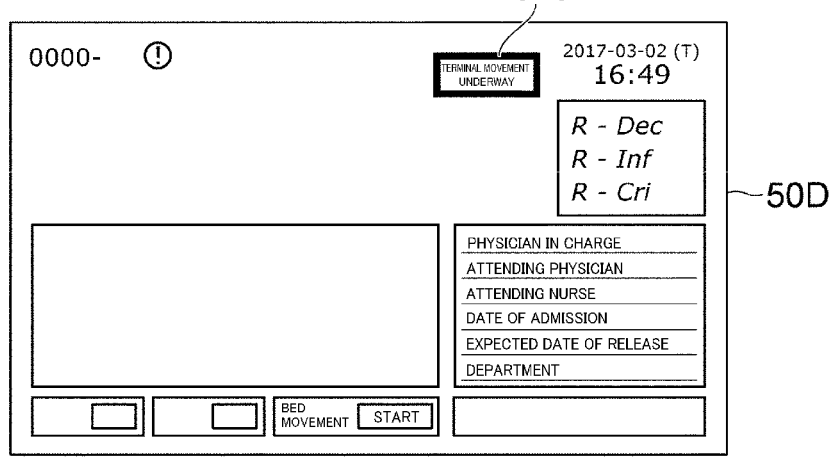

As shown in FIG. 10(a), a "start" "bed movement" button 81a (one region of the screen) is touched (or clicked). As a result, a "login screen" shown in FIG. 10(b) is displayed. An "ID" and a "password" are input on the login screen. As a result, a confirmation window shown in FIG. 10(c) is displayed. A "yes" button 81b (one region of the screen) relating to a confirmation message is touched (or clicked). As a result, the user interface device 55 shifts to a setting modification state (a "movement state"). At this time, as shown in FIG. 10(d), a "terminal movement underway" display 81c is displayed.

In this state, a power supply of the user interface device 55 is switched OFF. The user interface device 55 is then moved from ward "2201" to ward "0501".

Figure 11A:
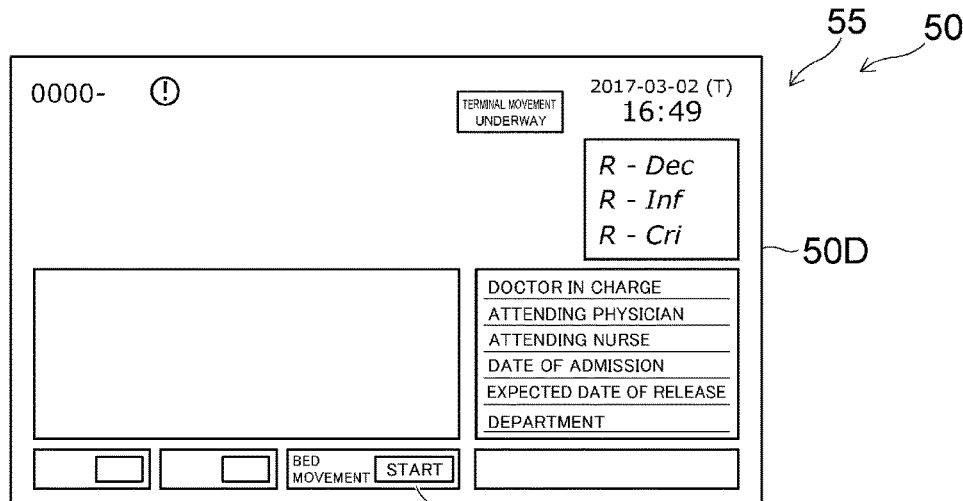
FIGS. 11(a) to 11(d) are pattern diagrams showing examples of displays displayed in a bed system according to an embodiment.
Figure 11B:
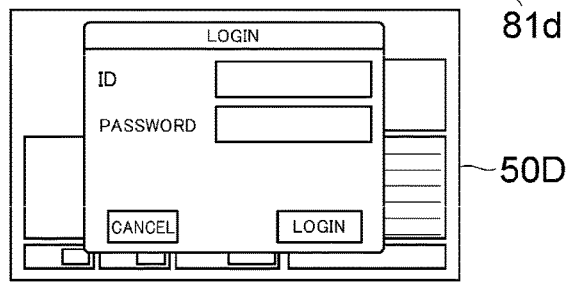
Figure 11C:
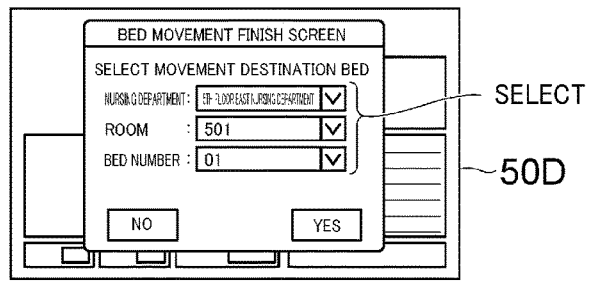
Figure 11D:
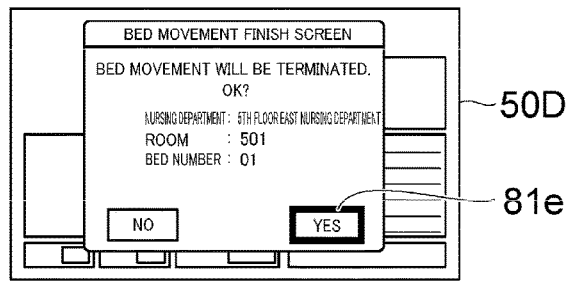

When movement is complete, the power supply of the user interface device 55 is switched ON. As a result, an image shown in FIG. 11(a) is displayed on the display 50D of the user interface device 55. A "start" "bed movement" button 81d (one region of the screen) is touched (or clicked). As a result, a "login screen" shown in FIG. 11(b) is displayed. An "ID" and a "password" are input on the login screen. As a result, an input window shown in FIG. 11(c) is displayed. A nursing department, a room, a bed number, and so on, for example, are received in the input window. For example, candidate names for each of the nursing department, the room, the bed number, and so on are displayed, and selections are made from the candidates. For example, the selections may be input. When input is complete, a confirmation window shown in FIG. 11(d) is displayed. In the confirmation window, a "yes" button 81e (one region of the screen) is touched (or clicked). As a result, the values (information) input in the input window are confirmed and stored in a storage unit, for example.

At this time, when the values (information) input in the input window of the user interface device 55 moved by the operation described above have already been set in another user interface device 55, a message indicating this may be displayed. Alternatively, the other user interface device 55 may be changed to the "terminal movement underway" state.

Figure 12:
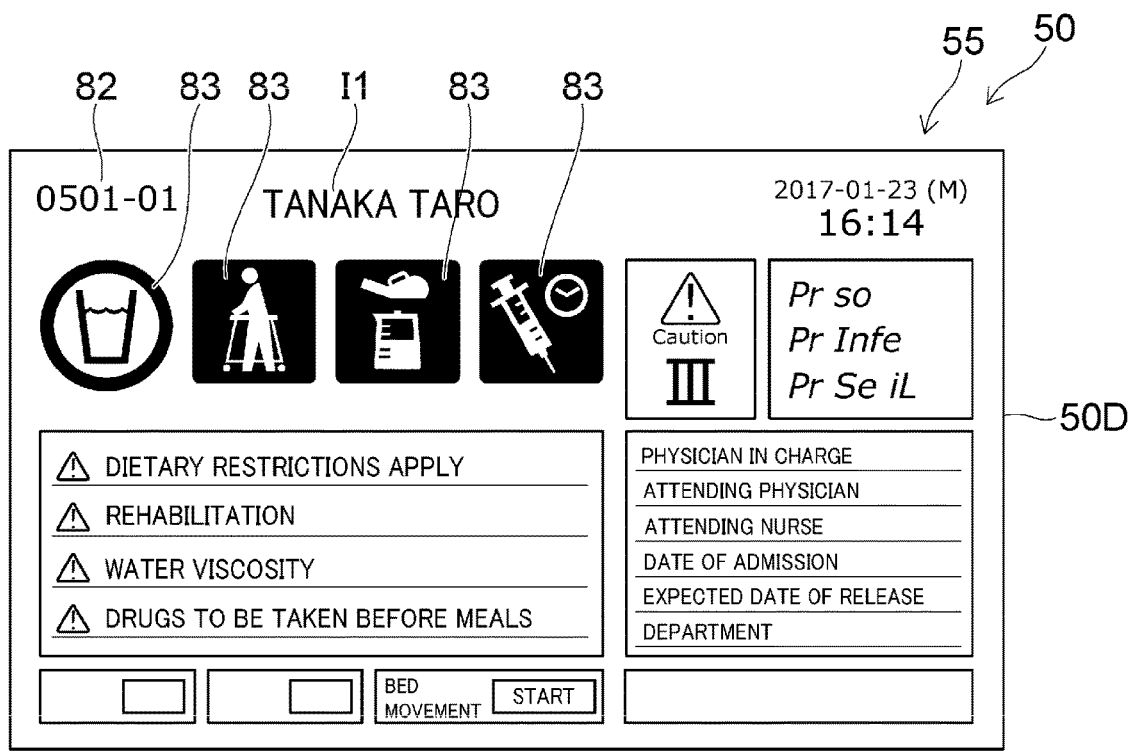
FIG. 12 is a pattern diagram showing an example of a display displayed in a bed system according to an embodiment.

When the post-movement settings are input correctly in the confirmation window described in relation to FIG. 11(d), an image shown in FIG. 12 is displayed. As shown in FIG. 12, identification information 82 indicating "0501" as the new ward is displayed. At this time, the identification information I1 specifying the user is also displayed.

As shown in FIG. 12, various types of information 83 (pictograms, for example) relating to the user may also be displayed. This information 83 is information relating to the care and so on provided to the user. The types of displayed information 83 may be configured to be modifiable using the user interface device 55.

Figure 13A:
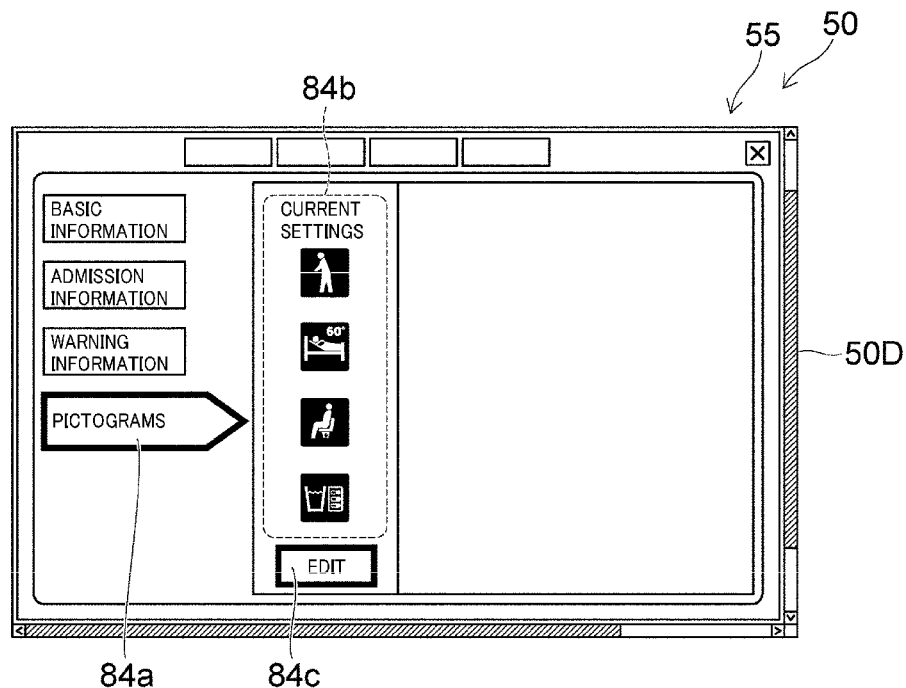
FIGS. 13(a) and 13(b) are pattern diagrams showing examples of displays displayed in a bed system according to an embodiment.
Figure 13B:
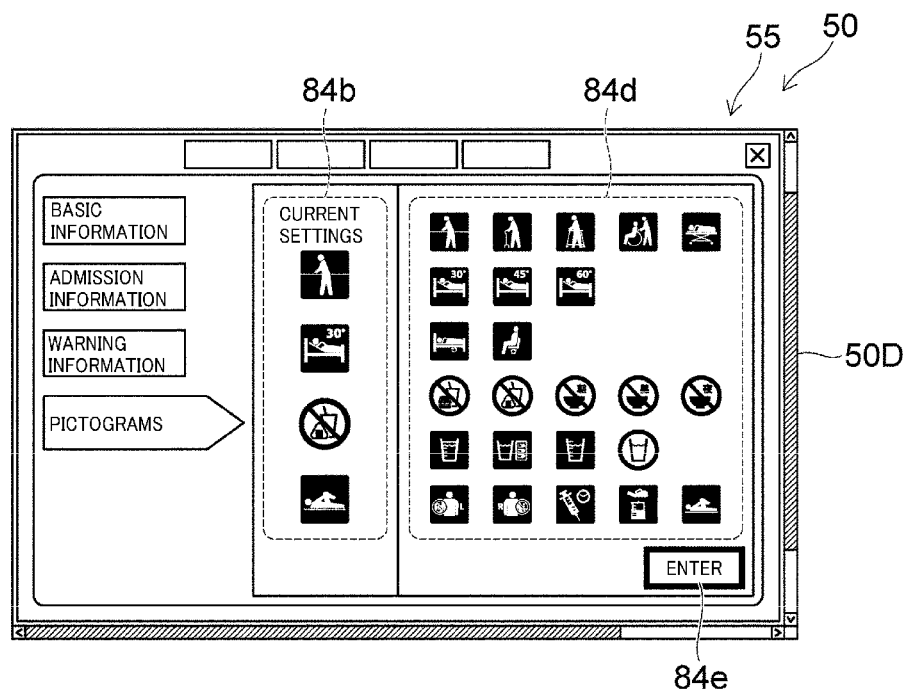

FIGS. 13(a) and 13(b) are pattern diagrams showing examples of displays displayed in a bed system according to an embodiment.

These figures show setting of the above information 83 (pictograms, for example) relating to the user.

As shown in FIG. 13(a), a confirmation/setting image is displayed on the display 50D of the user interface device 55. For example, when a "pictograms" button 84a (one region of the screen) is touched (or clicked), a confirmation/setting image is displayed in relation to "pictograms". In this example, four "pictograms" can be displayed. Information 84b relating to the four currently displayed "pictograms" is displayed. In this state, an "edit" button 84c (one region of the screen) is touched (or clicked). As a result, the display shifts to a selection image shown in FIG. 13(b).

As shown in FIG. 13(b), the selection image displays information 84d relating to a preset "pictogram group", for example. An operator of the user interface device 55 selects several of the pictograms in the "pictogram group". For example, when four "pictograms" can be displayed, the "pictograms" displayed heretofore are replaced with newly selected "pictograms". When selection is complete, an "enter" button 84e (one region of the screen) is touched (or clicked). As a result, the information 83 (pictograms, for example) displayed in relation to the user is modified.

An example of the first input/output device 60 will now be described.

Figure 14:
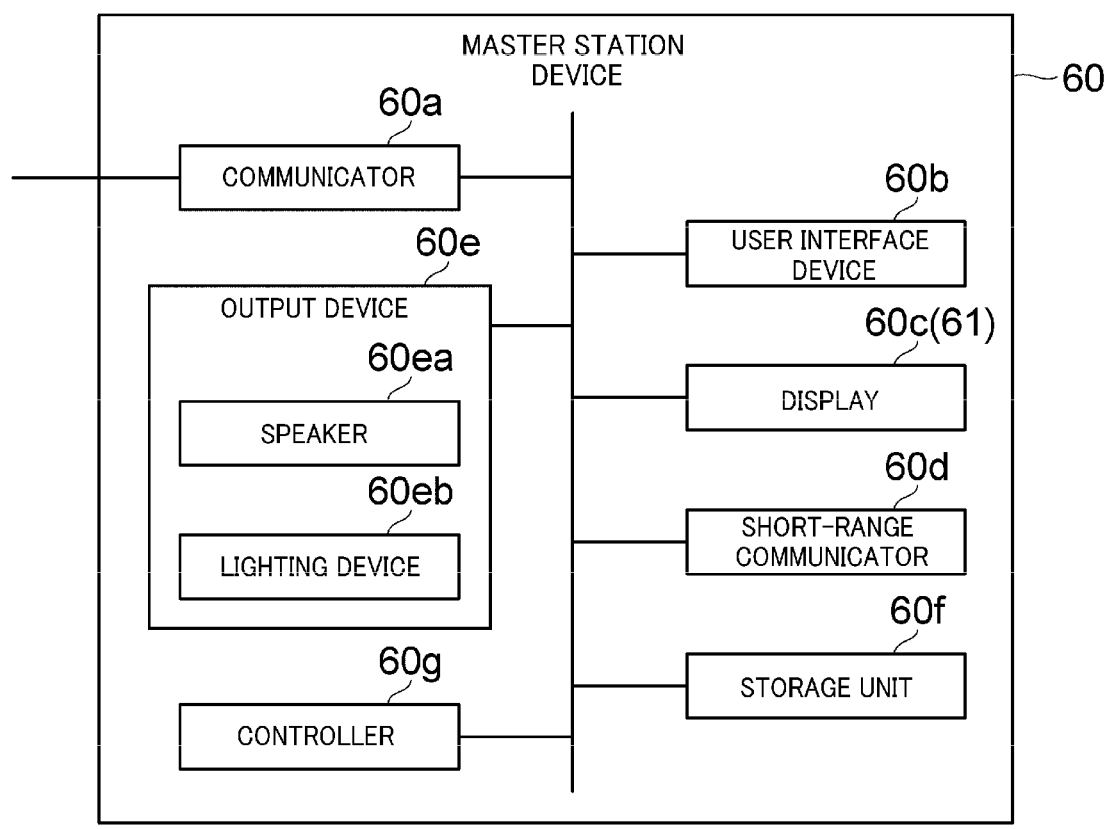
FIG. 14 is a pattern diagram showing an example of a part of a bed system according to an embodiment.

FIG. 14 is a pattern diagram showing an example of a part of a bed system according to an embodiment.

FIG. 14 is a block diagram of the first input/output device 60. As shown in FIG. 14, the first input/output device 60 includes, for example, a communicator 60a, a user interface device 60b (an input reception unit), a display 60c (the first display 61, for example), a short-range communicator 60d, an output device 60e, a storage unit 60f, and a controller 60g (a processing unit).

The communicator 60a includes a communication interface circuit, for example. The communicator 60a communicates with another device (the plurality of bed devices 50, for example) using a wired or wireless method selected as desired. For example, communication may be performed via the server 65.

The user interface device 60b includes a keyboard, a pointing device (a mouse, a tablet, or the like), and buttons or a touch panel, for example. The user interface device 60b receives input.

The display 60c includes a display device. The display 60c displays information, for example. The display 60c may display at least one of the notification display 30N and the warning display 30A, for example. The display 60c, the user interface device 60b, and the display 60c may be integrated.

The short-range communicator 60d communicates with various devices, for example. For example, communication is performed between an identification tag or the like carried by the caregiver or the like and the short-range communicator 60d. As a result, the caregiver or the like is identified and so on. Communication by the short-range communicator 60d is based on a wireless system, for example.

The output device 60e includes at least one of a speaker 60ea (a speaker or the like, for example) and a lighting device 60eb (a light-emitting element or the like, for example), for example. The output device 60e issues reports, for example.

The storage unit 60f includes a magnetic hard disk device, a semiconductor storage device, or the like, for example. The storage unit 60f stores the plurality of user interface device information 55i, for example. The storage unit 60f stores a program of the processing executed by the controller 60g and so on, for example.

The controller 60g includes an electronic circuit (a CPU: Central Processing Unit or the like, for example), for example. The controller 60g executes processing based on the program, for example. For example, the controller 60g compares the measurement values with the set values and so on, for example. The controller 60g then causes at least one of the display 60c and the output device 60e to issue a report in accordance with the comparison result.

Figure 15:
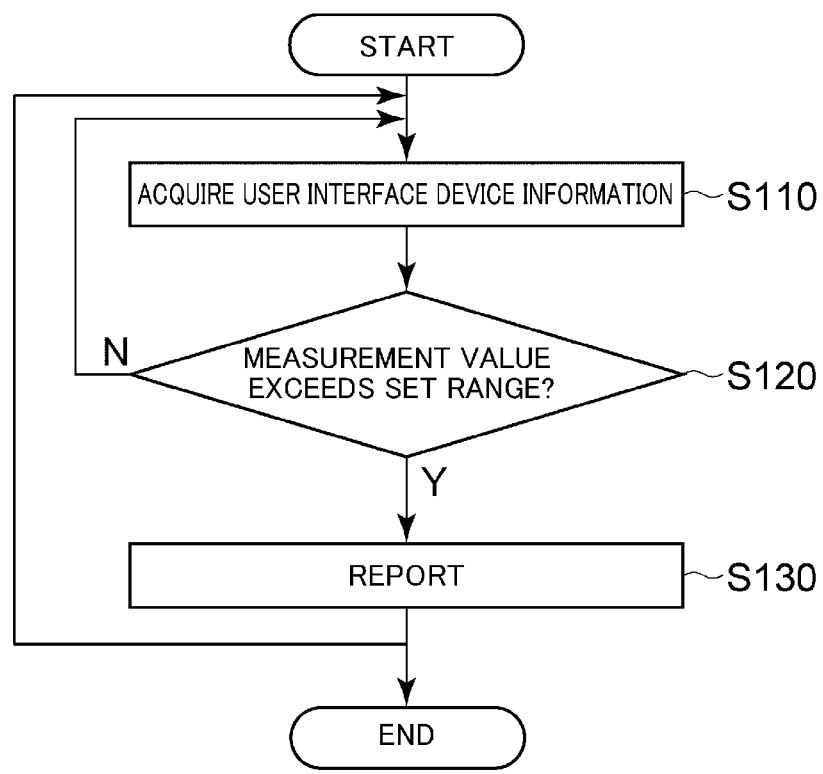
FIG. 15 is a flowchart showing an example of an operation performed in a bed system according to an embodiment.

FIG. 15 is a flowchart showing an example of an operation performed in a bed system according to an embodiment.

FIG. 15 shows an operation performed by a controller (the controller 60g, for example) according to an embodiment. For example, the controller 60g acquires the user interface device information 55i (step S110). The user interface device information 55i includes the measurement values of the plurality of items in the plurality of bed devices 50. The controller 60g determines whether or not the measurement values exceed set ranges (a range determined by the first set value, a range determined by the first set value, and so on) (step S120). When a measurement value exceeds a set range, the controller 60g causes another device (the display 60c, the output device 60e, or the like) to issue a report (step S130). The processing then returns to step S110. When the measurement values do not exceed the set ranges, on the other hand, the processing returns to step S110. By implementing this processing, reports are issued appropriately.

Examples of the user interface device 55, the second display 62, and the server 65 will be described below. FIG.

16 is a pattern diagram showing an example of a part of a bed system according to an embodiment.

Figure 16:
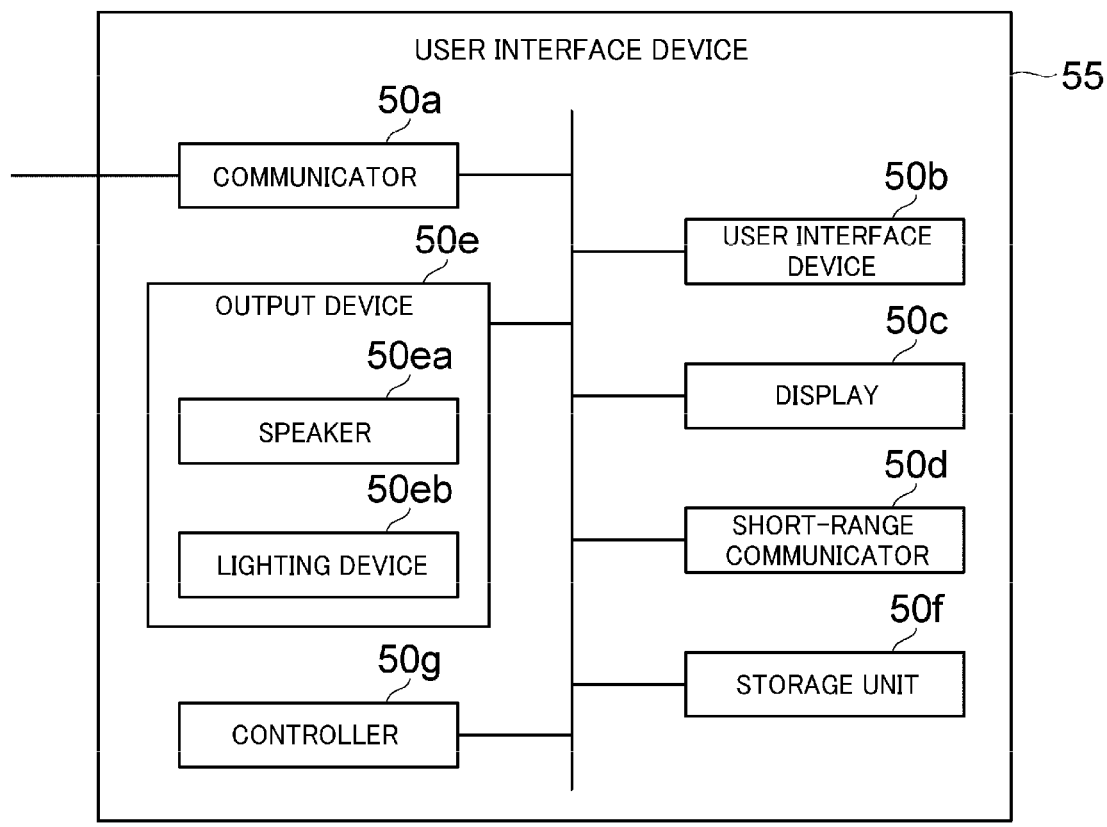
FIG. 16 is a pattern diagram showing an example of a part of a bed system according to an embodiment.

FIG. 16 is a block diagram of the user interface device 55. As shown in FIG. 16, the user interface device 55 includes, for example, a communicator 50a, a user interface device 50b (an input reception unit), a display 50c, a short-range communicator 50d, an output device 50e, a storage unit 50f, and a controller 50g (a processing unit). The output device 50e includes at least one of a speaker 50ea (a speaker or the like, for example) and a lighting device 50eb (a light-emitting element or the like, for example), for example.

Figure 17:
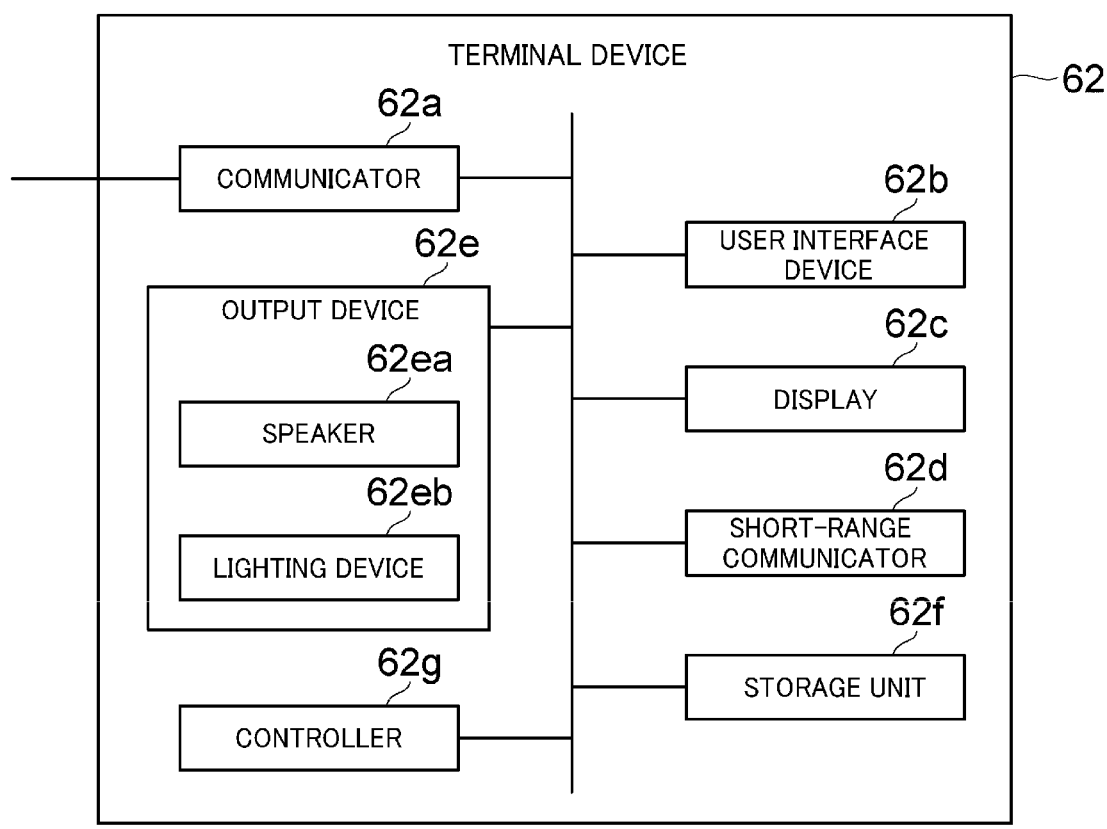
FIG. 17 is a pattern diagram showing an example of a part of a bed system according to an embodiment.

FIG. 17 is a pattern diagram showing an example of a part of a bed system according to an embodiment.

FIG. 17 is a block diagram of a terminal device including the second display 62. As shown in FIG. 17, the terminal device includes, for example, a communicator 62a, a user interface device 62b (an input reception unit), a display 62c, a short-range communicator 62d, an output device 62e, a storage unit 62f, and a controller 62g (a processing unit). The output device 62e includes at least one of a speaker 62ea (a speaker or the like, for example) and a lighting device 62eb (a light-emitting element or the like, for example), for example.

The configuration described in relation to the communicator 60a can be applied to the communicator 50a and the communicator 62a. The configuration described in relation to the user interface device 60b can be applied to the user interface device 50b and the user interface device 62b. The configuration described in relation to the display 60c can be applied to the display 50c and the display 62c. The configuration described in relation to the short-range communicator 60d can be applied to the short-range communicator 50d and the short-range communicator 62d. The configuration described in relation to the output device 60e can be applied to the output device 50e and the output device 62e. The configuration described in relation to the storage unit 60f can be applied to the storage unit 50f and the storage unit 62f. The configuration described in relation to the controller 60g can be applied to the controller 50g and the controller 62g. The controller 50g and the controller 62g may implement the operation (see FIG. 15) described in relation to the controller 60g.

The terminal device including the second display 62 may issue the report, for example. At least one of the plurality of user interface devices 55 may issue the report, for example. When one of the plurality of user interface devices 55 issues the report, a report relating to that user interface device 55 is issued.

Figure 18:
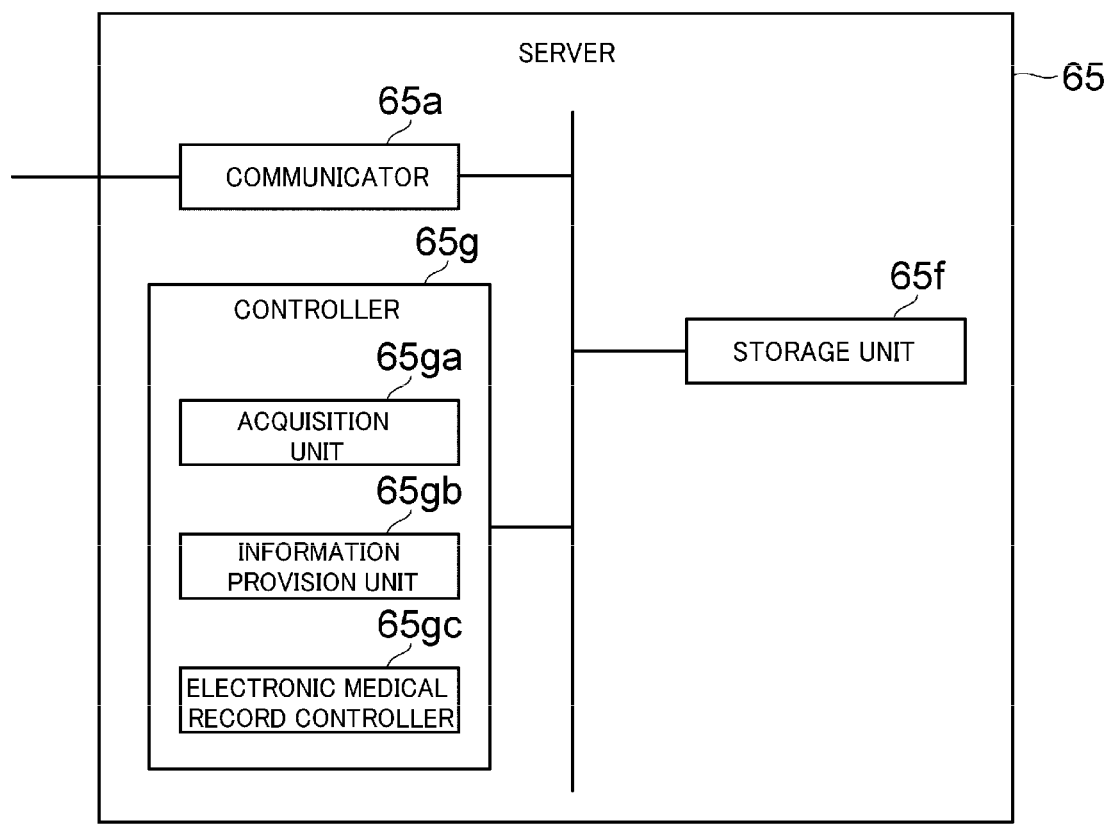
FIG. 18 is a pattern diagram showing an example of a part of a bed system according to an embodiment.

FIG. 18 is a pattern diagram showing an example of a part of a bed system according to an embodiment.

FIG. 18 is a block diagram of the server 65. As shown in FIG. 18, the server 65 includes, for example, a communicator 65a, a storage unit 65f, and a controller 65g (a processing unit). The controller 65g may include, for example, an acquisition unit 65ga, an information provision unit 65gb, an electronic medical record controller 65gc, and so on, for example.

The configuration described in relation to the communicator 60a can be applied to the communicator 65a. The configuration described in relation to the storage unit 60f can be applied to the storage unit 65f. The configuration described in relation to the controller 60g can be applied to the controller 65g. The controller 65g implements at least one of acquiring information from another device, providing information to another device, and controlling the electronic medical record storage unit 66, for example.

In the bed system 110 according to an embodiment, setting (notification setting, device setting, or the like) relating to a plurality of bedsides (various devices including the beds 51, as well as the users of the beds 51) can be implemented (input or edited) in a remote location, for example. When setting relating to a plurality of bedsides is implemented in a remote location, the following state, for example, may occur. For example, when setting is implemented without seeing the state of a bedside, setting that is inappropriate for the state of the bedside may be implemented. For example, when setting is implemented in relation to a large number of users, it may be difficult to notice that setting deviating from management standards of the facility (a hospital or the like) has been implemented. Thus, a setting error that is difficult to ascertain may occur. When setting (confirmation) is implemented in relation to a plurality of users all at once, the volume of display increases, and as a result, confirmation (setting) may take time. For example, when setting is implemented on a plurality of different terminals, simultaneous editing may occur, leading to unintended setting. It is desirable to suppress errors occurring during setting implemented in relation to a plurality of setting subjects (the beds 51 and the users). It is also desirable to be able to implement setting efficiently.

In an embodiment, setting relating to a plurality of bedsides can be implemented efficiently in a remote location, for example. For example, the user interface devices 55 collect information relating to the plurality of bed devices 50. The plurality of user interface device information 55i collected from the plurality of user interface devices 55 is supplied to the first input/output device 60. At this time, the information passes through the server 65, for example. The collected plurality of user interface device information 55i is supplied to the first input/output device 60, and the first input/output device 60 implements setting in relation to the plurality of bedsides. The set values relating to the plurality of bedsides may be viewed on the first input/output device 60.

The bed system 110 according to an embodiment may further include the server 65. The bed system 110 may further include the electronic medical record storage unit 66.

As described above, in the first embodiment, during the non-reception operation, the first input/output device 60 (a master station device, for example) does not receive input of the second set value relating to the second item 32 set in each of the plurality of bed devices (see FIGS. 2 and 3). The second item 32 relates to the user behavior information 52i relating to the user of the bed 51, for example. The user behavior information 52i includes at least one of bed departure, sleeping, waking up, sitting up, and sitting on the edge of the bed. For example, the first input/output device 60 (a master station device, for example), which is remote from the subject bed 51, does not receive input of the second set value. Meanwhile, the first input/output device 60 can display the second set value set in at least one of the plurality of bed devices 50 on the browsing mode display 61B, for example.

For example, when the bed departure notification changes from OFF to ON while the bed back angle is at a minimum or the bed height is at a minimum, in certain cases a part (the actuator) of the bed 51 may move slightly. When the bed departure notification setting is switched from OFF to ON in the first input/output device 60, which is remote from the bed 51, the user of the bed 51 may experience a sense of discomfort. At this time, according to the first embodiment, the first input/output device 60 does not receive input of the second set value relating to the second item 32, and therefore this sense of discomfort can be suppressed. For example, the second set value can be input while the caregiver or the like is present at the subject bed 51. For example, a sense of discomfort can be suppressed and a greater sense of security can be provided.

In an example of an embodiment, when, for example, the bed back angle is in a first state so as to be larger than a first angle and the bed height is in a second state so as to be higher than a first height, substantially no movement occurs in a part (the actuator) of the bed 51 even if the bed departure notification changes from OFF to ON. The first angle is a small angle, for example. In one example, the first angle is the minimum angle of the bed 51. In one, the first angle is no more than 5 degrees. The first height is a low height. In one example, the first height is the minimum height of the bed 51. In one example, the first height is no more than 30 cm.

In an example of an embodiment, when the back angle of the bed 51 is in the first state so as to be larger than the first angle and the bed height is in the second state so as to be higher than the first height, the first input/output device 60 receives input of the set values relating to the items set in the aforesaid one of the plurality of bed devices 50. When the back angle is not in the first state and/or the bed height is not in the second state, the first input/output device 60 does not receive input of the set value.

In another example of an embodiment, when the bed back angle is in the first state so as to be larger than the first angle, substantially no movement occurs in a part of the bed 51 even if the notification relating to the user sitting up changes from OFF to ON. In this case, for example, when the back angle of the bed 51 is in the first state so as to be larger than the first angle, the first input/output device 60 receives input of the set values relating to the items set in the aforesaid one of the plurality of bed devices 50. For example, when the bed height is in the second state so as to be higher than the first height, substantially no movement occurs in a part of the bed 51 even if the bed departure notification changes from OFF to ON. In this case, for example, the first input/output device 60 receives input of the set values relating to the items set in the aforesaid one of the plurality of bed devices 50. When the back angle is not in the first state and the height is not in the second state, the first input/output device 60 does not receive input of the set value.

Figure 19:
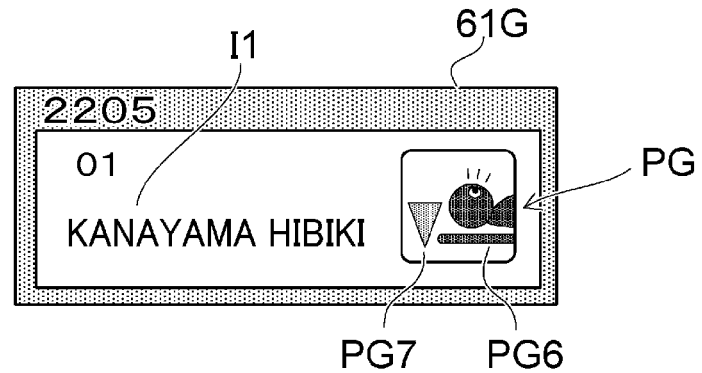
FIG. 19 is a pattern diagram showing an example of an image displayed in a bed system according to an embodiment.

FIG. 19 is a pattern diagram showing an example of an image displayed in a bed system according to an embodiment.

FIG. 19 shows an example of one of the plurality of images 61G. As shown in FIG. 19, a pictogram PG includes a graphic PG6 relating to the back section 70*a* and a graphic PG7 relating to the height of the bed 51 (the section), for example. The graphic PG6 indicates that the back section 70*a* is at the minimum (an angle of 0 degrees), for example. The graphic PG7 indicates that the height of the bed 51 is at the minimum. The pictogram PG may include various graphics indicating the state of the bed 51. As shown in FIG. 19, when the back section 70*a* is at the minimum (an angle of 0 degrees) (i.e. not in the first state), the first input/output device 60 does not receive input of the second set value. When the height of the bed 51 is at the minimum (i.e. not in the second state), the first input/output device 60 does not receive input of the second set value.

Furthermore, in an embodiment, the first input/output device 60 may receive a setting for switching a notification relating to the second item 32 from ON to OFF. At this time, the first input/output device 60 does not receive a setting for switching the notification relating to the second item 32 from OFF to ON. For example, when the bed departure notification is modified from ON to OFF, substantially no movement occurs in a part (the actuator) of the bed 51. Therefore, when the notification is modified from ON to OFF, the first input/output device 60, which is remote from the bed 51, may receive the setting modification (input of the second set value).

FIG. 20 is a pattern diagram showing an example of a display screen displayed in a bed system according to an embodiment. FIG. 20 shows an example of the editing mode display 61E. FIG. 20 corresponds to FIG. 3. In the example shown in FIG. 20, when the bed back angle is in the first state, the first input/output device 60 can receive input of the second set value. When the bed height is in the second state, the first input/output device 60 can receive input of the second set value. When the bed back angle is at the minimum, on the other hand, the first input/output device 60 does not receive input of the second set value. When the bed height is at the minimum, the first input/output device 60 does not receive input of the second set value.

In the example shown in FIG. 20, in the bed 51 corresponding to "user number 01 on ward 2224", the bed back angle is not at the minimum and the bed height is not at the minimum. At this time, the first input/output device 60 can receive input of the second set value. In the example shown in FIG. 20, a region corresponding to the second item 32 in relation to "user number 01 on ward 2224" is white (a light image).

In the example shown in FIG. 20, in the beds 51 corresponding to "user numbers 02 to 04 on ward 2224" and "user numbers 01 to 03 on ward 2225", the bed back angle is not in the first state and the bed height is not in the second state. At this time, the first input/output device 60 does not receive input of the second set value. In the example shown in FIG. 20, regions corresponding to the second item 32 in relation to these users are gray (dark images displayed by dots in FIG. 20). Whether or not reception is possible can be recognized easily by employing light images and dark images, for example.

Figure 21A:
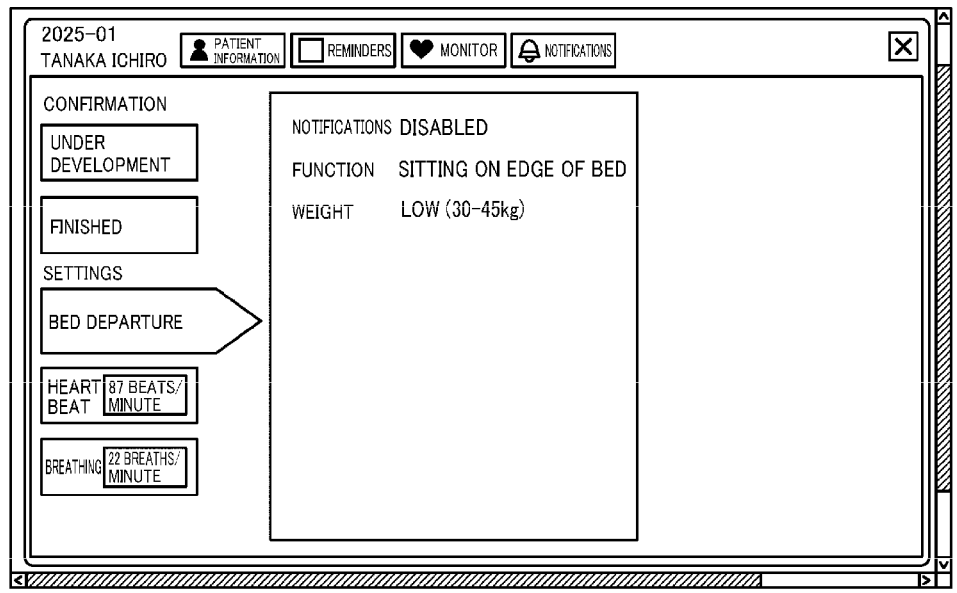
FIGS. 21(a) and 21(b) are pattern diagrams showing examples of display screens displayed in a bed system according to an embodiment.
Figure 21B:
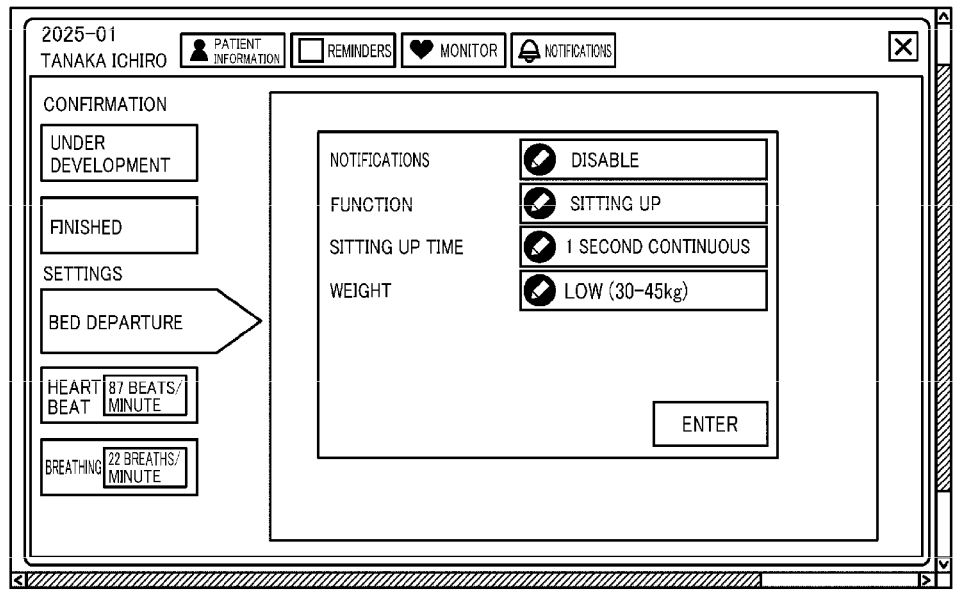

FIGS. 21(*a*) and 21(*b*) are pattern diagrams showing examples of display screens displayed in a bed system according to an embodiment.

These figures show examples of various setting screens relating to the users corresponding respectively to the plurality of beds 51. FIG. 21(*a*) corresponds to a case in which setting input cannot be received. For example, FIG. 21(*a*) corresponds to a case in which the bed back angle is not in the first state and the bed height is not in the second state. FIG. 21(*b*) corresponds to a case in which setting input can be received. For example, FIG. 21(*b*) corresponds to a case in which the bed back angle is in the first state and the bed height is in the second state.

As shown in FIG. 21(*a*), with respect to "bed departure", the state can be viewed. As shown in FIG. 21(*b*), meanwhile, with respect to "bed departure", for example, the "notification" can be enabled or disabled, the "function" can be set, the "sitting up time" can be set, and the "weight" can be set (input).

In this example, the bed system 110 includes the plurality of bed devices 50 and the first input/output device 60 capable of communicating with the plurality of bed devices 50. One of the plurality of bed devices 50 includes the bed 51. When the back angle of the bed 51 is not at the minimum and the height of the bed 51 is not at the minimum, the first input/output device 60 can receive input of a set value (the second set value, for example) relating to an item (the second item 32, for example) set in the aforesaid one of the plurality of bed devices 50. When the back angle of the bed 51 is at the minimum and the height of the bed 51 is at the minimum, the first input/output device 60 does not receive input of the set value (the second set value, for example). At least one of the first input/output device 60 and the aforesaid one of the plurality of bed devices implements an operation corresponding to the set value.

The aforesaid item is the second item 32, for example. The aforesaid item relates to user behavior information including at least one of bed departure, sleeping, waking up, sitting up, and sitting on the edge of the bed in relation to the user of the bed 51, for example.

An embodiment may include the following configurations (concepts, for example).

(Configuration 1)

A bed system including:

a plurality of bed devices; and a first input/output device capable of communicating with the plurality of bed devices, wherein the first input/output device implements a first operation, during the first operation, the first input/output device receives input of a first set value relating to a first item set in each of the plurality of bed devices, and at least one of the first input/output device and the plurality of bed devices implements an operation corresponding to the first set value.

(Configuration 2)

The bed system according to configuration 1, wherein the first input/output device further implements a second operation, during the second operation, the first input/output device implements either a non-reception operation or a reception operation, in the non-reception operation, the first input/output device does not receive input of a second set value relating to a second item set in each of the plurality of bed devices, in the reception operation, the first input/output device receives input of the second set value, and the at least one of the first input/output device and the plurality of bed devices implements an operation corresponding to the second set value after at least one of the plurality of bed devices receives approval of the second set value following the reception operation.

(Configuration 3)

The bed system according to configuration 2, wherein one bed device among the plurality of bed devices includes:

a bed; and a bed input/output unit connected to the bed, and the bed input/output unit is capable of receiving input of the first set value of the one bed device among the plurality of bed devices and input of the second set value of the one bed device among the plurality of bed devices.

(Configuration 4)

The bed system according to configuration 3, wherein the first item relates to at least one of a heartbeat of a user of the bed and breathing of the user.

(Configuration 5)

The bed system according to configuration 4, wherein the heartbeat of the user and the breathing of the user are acquired from the bed or an auxiliary device of the bed.

(Configuration 6)

The bed system according to configuration 3, wherein the second item relates to user behavior information including at least one of bed departure, sleeping, waking up, sitting up, and sitting on the edge of the bed in relation to a user of the bed.

(Configuration 7)

The bed system according to any one of configurations 3 to 6, wherein, when the bed input/output unit receives input of a different set value relating to the first item while the first input/output device implements the first operation, the at least one of the first input/output device and the plurality of bed devices implements an operation corresponding to the different set value.

(Configuration 8)

The bed system according to any one of configurations 2 to 7, wherein the first input/output device implements the non-reception operation, and the first input/output device displays the second set value set in at least one of the plurality of bed devices.

(Configuration 9)

The bed system according to any one of configurations 2 to 8, wherein the first input/output device implements the reception operation, and the at least one of the plurality of bed devices issues a notification prompting approval of implementation of the operation corresponding to the second set value.

(Configuration 10)

The bed system according to any one of configurations 2 to 9, wherein the first input/output device, during the reception operation, issues a notification indicating that the second set value has not yet been approved.

(Configuration 11)

The bed system according to any one of configurations 2 to 10, further including a separate bed device not connected to the first input/output device, wherein the first input/output device displays information relating to the plurality of bed devices on a single screen but does not display information relating to the separate bed device on the single screen.

(Configuration 12)

The bed system according to any one of configurations 2 to 11, wherein the first input/output device issues a notification when at least one of the first set value and the second set value exceeds a reference range.

(Configuration 13)

The bed system according to any one of configurations 1 to 12, wherein the first input/output device acquires a first measurement value relating to the first item from one of the plurality of bed devices in which the first set value has been set, and the operation corresponding to the first set value includes issuing a report when the measurement value exceeds a range determined by the first set value.

(Configuration 14)

A bed system including:

a plurality of bed devices; and a storage unit, wherein one bed device among the plurality of bed devices includes:

a bed; and a bed input/output unit connected to the bed and provided separately to the bed, the bed input/output unit is capable of acquiring state information, the state information includes at least one of bed state information relating to the bed and user state information relating to the state of a user of the bed, the bed state information includes bed moving part information relating to at least one of a height and an angle of the bed, the user state information includes at least one of vital signs information relating to the user and user behavior information relating to the user, the vital signs information includes information relating to at least one of a blood pressure, a blood oxygen saturation, a blood glucose level, a heart rate, a pulse rate, a respiration rate, a weight, and a body temperature of the user, the user behavior information includes information relating to at least one of bed departure, sleeping, waking up, sitting up, and sitting on the edge of the bed in relation to the user, and the storage unit stores at least a part of the state information acquired by the bed input/output unit in association with at least one of identification information specifying the user and identification information specifying the bed input/output unit.

(Configuration 15)

The bed system according to configuration 14, wherein the bed input/output unit is capable of displaying the identification information specifying the user and the identification information specifying the bed input/output unit, and the bed input/output unit implements an operation for prompting approval of a correspondence relationship between the identification information specifying the user and the identification information specifying the bed input/output unit.

(Configuration 16)

A bed system including:

a plurality of bed devices; and a first input/output device capable of communicating with the plurality of bed devices, wherein one bed device among the plurality of bed devices includes a bed, when a back angle of the bed is in a first state so as to be larger than a first angle and a height of the bed is in a second state so as to be higher than a first height, the first input/output device receives input of a set value relating to an item set in the one bed device among the plurality of bed devices, when the back angle is not in the first state and/or the height is not in the second state, the first input/output device does not receive input of the set value, and the at least one of the first input/output device and the plurality of bed devices implements an operation corresponding to the set value.

(Configuration 17)

A bed system including:

a plurality of bed devices; and a first input/output device capable of communicating with the plurality of bed devices, wherein one bed device among the plurality of bed devices includes a bed, when a back angle of the bed is in a first state so as to be larger than a first angle and/or a height of the bed is in a second state so as to be higher than a first height, the first input/output device receives input of a set value relating to an item set in the one bed device among the plurality of bed devices, when the back angle is not in the first state and the height is not in the second state, the first input/output device does not receive input of the set value, and the at least one of the first input/output device and the plurality of bed devices implements an operation corresponding to the set value.

(Configuration 18)

The bed system according to any one of configurations 1 to 17, wherein the item relates to user behavior information including at least one of bed departure, sleeping, waking up, sitting up, and sitting on the edge of the bed in relation to a user of the bed.

According to this embodiment, a bed system having improved usability can be provided.

Embodiments of the present invention were described above with reference to specific examples. However, the present invention is not limited to these specific examples. For example, a person skilled in the art could implement the present invention similarly by selecting appropriate, well-known configurations as specific configurations of the respective elements, such as the plurality of bed devices and the first input/output device, included in the bed system, and as long as similar effects are obtained as a result, these configurations are included in the scope of the present invention.

Components obtained by combining two or more elements of the specific examples within a technically feasible scope are also included within the scope of the present invention, provided these components encompass the gist of the present invention.

In addition, all bed systems that could be realized by a person skilled in the art by implementing appropriate design modifications on the basis of the bed system described above as an embodiment of the present invention are likewise included in the scope of the present invention, provided these bed systems encompass the gist of the present invention.

Furthermore, a person skilled in the art could arrive at various modified and amended examples within the scope of the spirit of the present invention, and these modified and amended examples are also included within the scope of the present invention.

REFERENCE SIGNS LIST

30A Warning display
30Aa Distinctively shaped pattern
30N Notification display
31 First item
31a Column
31aB Cell
31aE Cell
31b Column
31bB Cell
31bE Cell
32 Second item
32B Cell
32E Cell
34 Button
50 Bed device
50D Display
50DM, 50DMA Message
50a Communicator
50b User interface device
50c Display
50d Short-range communicator
50e Output device
50ea Speaker
50eb Lighting device
50f Storage unit
50g Controller
51, 51A to 51C Bed
51i Bed moving part information
52, 52A to 52C Auxiliary device
52i User behavior information
53, 53A to 53C Measurement device 53a Blood pressure gauge
53b Pulse oximeter
53c Thermometer
53d Blood glucose meter
53i Measurement information
55, 55A to 55C User interface device
55i, 55iA to 55iC User interface device information
60 First input/output device
60a Communicator
60b User interface device
60c Display
60d Short-range communicator
60e Output device
60ea Speaker
60eb Lighting device
60f Storage unit
60g Controller
61 First display
61B Browsing mode display
61Ba Button
61D Screen
61E Editing mode display
61Ea Button
61Eb Button
61G Image
61H Window region
61I Acquisition unit
61M Message region
61e End button
62 Second display
62a Communicator
62b User interface device
62c Display
62d Short-range communicator
62e Output device
62ea Speaker
62eb Lighting device
62f Storage unit
62g Controller
65 Server
65a Communicator
65f Storage unit
65g Controller
65ga Acquisition unit
65gb Information provision unit
65gc Electronic medical record controller
66 Electronic medical record storage unit
70 Moving part
70a Back section
70b Knee section
70c Leg section
70d Height modifying part
81a Button
81b Button
81c Display
81d Button
81e Button
82 Identification information
83 Information
84a Button
84b Information
84c Button
84d Information
84e Button
110 Bed system
I0 User information
I1 Identification information
I2 Vital signs information
IB1 User interface device identification information
IC1 Attribute information
R1 to R3 First to third partial regions
R4 Outer edge partial region
R5 Background region

The invention claimed is:

1. A system comprising:
a plurality of first devices associated to a plurality of beds, respectively, one of the first devices being capable of setting a first value of a first item for a first bed of the plurality of beds and a second value of a second item for the first bed, the first item being different from the second item; and
a second device capable of communicating with the first devices, the second device being capable of receiving input for setting the first value of the first item, the second device being capable of receiving a first instruction to change the first value to a third value,
wherein only the one of the first devices is capable of changing the second value of the second item to a fourth value, and the second device is not capable of receiving a second instruction to change the second value to the fourth value.

2. The bed system according to claim 1, wherein the plurality of beds are respectively connected to the first devices, and the one of the first devices is provided adjacent to the first bed.

3. The bed system according to claim 1, wherein the second device acquires a measurement value relating to the first item, and
the second device issues a report when the third value is set and the measurement value exceeds a range determined by the third value.

4. A system comprising:
a plurality of first devices associated to a plurality of beds, respectively, one of the first devices being capable of setting a first value of a first item for a first bed of the plurality of beds and a second value of a second item for the first bed, the first item being different from the second item; and
a second device capable of communicating with the first devices, the second device being capable of receiving input for setting the first value of the first item, the second device being capable of receiving a first instruction to change the first value to a third value,
wherein the second device includes a first mode and a second mode,
wherein in the first mode, the second device is not capable of receiving a second instruction to change the second value to a fourth value, and
wherein in the second mode, the second device is capable of receiving the second instruction to change the second value to the fourth value.

5. The bed system according to claim 4,
wherein when the second device is in the second mode, the second device changes the second value to the fourth value upon receiving approval from the one of the first devices of using the fourth value.

6. The bed system according to claim 5, wherein the first item relates to at least one of a heartbeat of a user of the first bed and breathing of the user.

7. The bed system according to claim 6, wherein the heartbeat of the user and the breathing of the user are acquired from the first bed or an auxiliary device of the first bed.

8. The bed system according to claim 7, wherein the second item relates to user behavior information including at least one of whether the user is staying in the first bed or the user gets out of the first bed, whether the user is sleeping or waking up, and whether the user is sitting up in a center of the first bed or sitting on an edge of the first bed.

9. The bed system according to claim 5, wherein, when the second device receives the first instruction to change the first value to the third value while the one of the first devices corresponding to the first bed receives a third instruction to change the first value to a fifth value, the fifth value being different from the third value, at least one of the second device and the one of the first devices corresponding to the first bed activates an alarm to indicate an error.

10. The bed system according to claim 5, wherein when the second device is in the second mode, the second device can show a notification indicating that the fourth value has not yet been approved.

11. The bed system according to claim 4, wherein when the second device is in the first mode, the second device can display the fourth value.

12. The bed system according to claim 4, further comprising:
a separate device not connected to the second device,
wherein the second device displays information relating to the first devices on a single screen but does not display information relating to the separate device on the single screen.

13. The bed system according to claim 4, wherein the second device determines whether at least one of the third value and the fourth value deviates from a reference range.

14. A bed system comprising:
a plurality of first devices; and
a second device capable of communicating with the plurality of first devices,
wherein one first device among the plurality of first devices includes a bed, a first controller, and a first user interface unit being capable of receiving an input,
wherein the second device includes a second controller and a second user interface unit being capable of receiving an input,
wherein the second user interface unit is configured to receive, from the one first device, the input for setting a value relating to an item set in the one first device when a back angle of the bed is in a first state so as to be larger than a first angle or a height of the bed is in a second state so as to be higher than a first height, and the second controller is configured to perform an operation corresponding to the set value, and
wherein the first user interface unit is configured to receive input of the set value and the first controller is configured to perform an operation corresponding to the set value when the back angle is not in the first state and the height is not in the second state, and the second user interface unit is configured to not receive input of the set value when the back angle is not in the first state and the height is not in the second state.

15. The bed system according to claim 14, wherein the item relates to user behavior information including at least one of whether a user of the bed is staying in the bed or the user gets out of the bed, whether the user is sleeping or waking up, and whether the user is sitting up in a center of the bed or sitting on an edge of the bed.

\* \* \* \* \*